United States Patent
Ding et al.

(10) Patent No.: US 11,406,409 B2
(45) Date of Patent: Aug. 9, 2022

(54) EXTENDABLE LENGTH SURGICAL INSTRUMENTS

(71) Applicant: COVIDIEN LP, Mansfield, MA (US)

(72) Inventors: Weijiang Ding, Shanghai (CN); Weisheng Lu, Jiangxi (CN); Jianjiang Chen, Shanghai (CN); Peng Yi, Shanghai (CN)

(73) Assignee: Covidien LP, Mansfield, MA (US)

( * ) Notice: Subject to any disclaimer, the term of this patent is extended or adjusted under 35 U.S.C. 154(b) by 306 days.

(21) Appl. No.: 15/509,074

(22) PCT Filed: Sep. 25, 2014

(86) PCT No.: PCT/CN2014/087425
§ 371 (c)(1),
(2) Date: Mar. 6, 2017

(87) PCT Pub. No.: WO2016/045049
PCT Pub. Date: Mar. 31, 2016

(65) Prior Publication Data
US 2017/0273703 A1    Sep. 28, 2017

(51) Int. Cl.
*A61B 17/29*  (2006.01)
*A61B 18/14*  (2006.01)
(Continued)

(52) U.S. Cl.
CPC ...... *A61B 17/2909* (2013.01); *A61B 18/1445* (2013.01); *A61B 34/35* (2016.02);
(Continued)

(58) Field of Classification Search
CPC .. A61B 2018/00196; A61B 2018/1455; A61B 2018/1452; A61B 2017/00995;
(Continued)

(56) References Cited

U.S. PATENT DOCUMENTS 5,275,614 A * 1/1994 Haber ............... A61B 17/0469
606/139
5,403,342 A * 4/1995 Tovey ................... A61B 17/29
600/104
(Continued)

FOREIGN PATENT DOCUMENTS

CN    1736339 A    2/2006
CN    102772237 A   11/2012
(Continued)

OTHER PUBLICATIONS

Chinese Office Action issued in corresponding Chinese Application No. 201480082107.3 dated Jan. 30, 2019, 17 pages.

*Primary Examiner* — Eun Hwa Kim
*Assistant Examiner* — Catherine Premraj
(74) *Attorney, Agent, or Firm* — Carter, DeLuca & Farrell LLP

(57) ABSTRACT

A surgical instrument includes a housing, a shaft coupled to and extending distally from the housing, an end effector assembly disposed at a distal end of the shaft, a movable handle coupled to the housing, a drive assembly coupled to the end effector assembly, and an extension mechanism disposed within the housing. The extension mechanism is configured to couple to the shaft and between the movable handle and the drive assembly for moving the shaft and drive assembly between a retracted position and an extended position relative to the housing. The extension mechanism is coupled between the movable handle and the drive assembly in each of the retracted and extended positions such that the movable handle is operable to effect manipulation of the end effector assembly in each of the retracted and extended positions.

21 Claims, 19 Drawing Sheets

(51) Int. Cl.
    *A61B 17/00*    (2006.01)
    *A61B 18/00*    (2006.01)
    *A61B 34/35*    (2016.01)

(52) U.S. Cl.
    CPC .............. *A61B 2017/00991* (2013.01); *A61B 2017/2901* (2013.01); *A61B 2018/00196* (2013.01); *A61B 2018/00202* (2013.01); *A61B 2018/00428* (2013.01); *A61B 2018/00607* (2013.01); *A61B 2018/1455* (2013.01)

(58) Field of Classification Search
    CPC . A61B 17/2909; A61B 18/1445; A61B 34/35; A61B 2017/00991; A61B 2017/2901; A61B 2018/00202; A61B 2018/00428; A61B 2018/00607
    See application file for complete search history.

(56) References Cited

U.S. PATENT DOCUMENTS

| | | | |
|---|---|---|---|
| 5,564,615 A | 10/1996 | Bishop et al. | |
| 5,662,662 A | 9/1997 | Bishop et al. | |
| H1745 H | 8/1998 | Paraschac | |
| 5,865,361 A | 2/1999 | Milliman et al. | |
| H1904 H | 10/2000 | Yates et al. | |
| H2037 H | 7/2002 | Yates et al. | |
| 7,799,028 B2 * | 9/2010 | Schechter | A61B 18/1445 606/205 |
| 8,328,822 B2 | 12/2012 | Huitema | A61B 17/10 606/142 |
| 9,084,608 B2 | 7/2015 | Larson et al. | |
| 9,211,657 B2 | 12/2015 | Ackley et al. | |
| 2004/0143240 A1 * | 7/2004 | Armstrong | A61M 25/00 604/528 |
| 2004/0254573 A1 | 12/2004 | Dycus et al. | |
| 2009/0326537 A1 * | 12/2009 | Anderson | A61B 17/17 606/80 |
| 2010/0292712 A1 | 11/2010 | Nering et al. | |
| 2011/0276049 A1 | 11/2011 | Gerhardt | |
| 2013/0060250 A1 * | 3/2013 | Twomey | A61B 18/1447 606/52 |
| 2013/0296922 A1 * | 11/2013 | Allen, IV | A61B 18/1445 606/205 |
| 2013/0296923 A1 | 11/2013 | Twomey et al. | |
| 2014/0221995 A1 | 8/2014 | Guerra et al. | |
| 2014/0221999 A1 | 8/2014 | Cunningham et al. | |
| 2014/0228842 A1 | 8/2014 | Dycus et al. | |
| 2014/0230243 A1 | 8/2014 | Roy et al. | |
| 2014/0236149 A1 | 8/2014 | Kharin et al. | |
| 2014/0243811 A1 | 8/2014 | Reschke et al. | |
| 2014/0243824 A1 | 8/2014 | Gilbert | |
| 2014/0249528 A1 | 9/2014 | Hixson et al. | |
| 2014/0250686 A1 | 9/2014 | Hempstead et al. | |
| 2014/0257274 A1 | 9/2014 | Mccullough, Jr. et al. | |
| 2014/0257283 A1 | 9/2014 | Johnson et al. | |
| 2014/0257284 A1 | 9/2014 | Artale | |
| 2014/0257285 A1 | 9/2014 | Moua | |
| 2014/0276803 A1 | 9/2014 | Hart | |
| 2014/0284313 A1 | 9/2014 | Allen, IV et al. | |
| 2014/0288549 A1 | 9/2014 | Mckenna et al. | |
| 2014/0288553 A1 | 9/2014 | Johnson et al. | |
| 2014/0330308 A1 | 11/2014 | Hart et al. | |
| 2014/0336635 A1 | 11/2014 | Hart et al. | |
| 2014/0353188 A1 | 12/2014 | Reschke et al. | |
| 2015/0018816 A1 | 1/2015 | Latimer | |
| 2015/0025528 A1 | 1/2015 | Arts | |
| 2015/0032106 A1 | 1/2015 | Rachlin | |
| 2015/0051598 A1 | 2/2015 | Orszulak et al. | |
| 2015/0051640 A1 | 2/2015 | Twomey et al. | |
| 2015/0066026 A1 | 3/2015 | Hart et al. | |
| 2015/0080880 A1 | 3/2015 | Sartor et al. | |
| 2015/0080889 A1 | 3/2015 | Cunningham et al. | |
| 2015/0082928 A1 | 3/2015 | Kappus et al. | |
| 2015/0088122 A1 | 3/2015 | Jensen | |
| 2015/0088126 A1 | 3/2015 | Duffin et al. | |
| 2015/0088128 A1 | 3/2015 | Couture | |
| 2015/0094714 A1 | 4/2015 | Lee et al. | |

FOREIGN PATENT DOCUMENTS

| | | | |
|---|---|---|---|
| CN | 103381104 A | 11/2013 | |
| CN | 103505282 A | 1/2014 | |
| WO | WO-2014156352 A1 * | 10/2014 | ......... A61B 17/3417 |

* cited by examiner

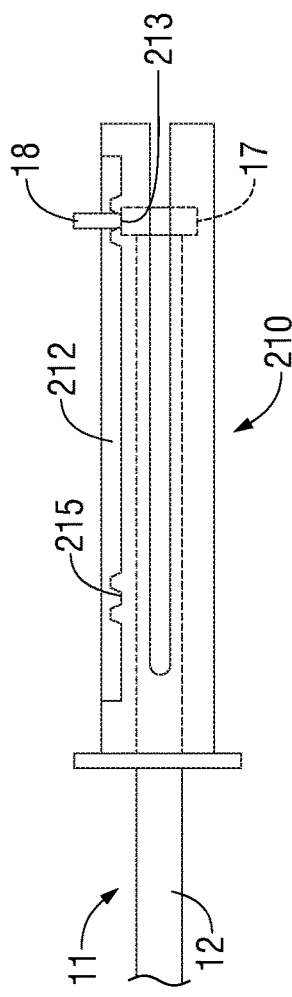
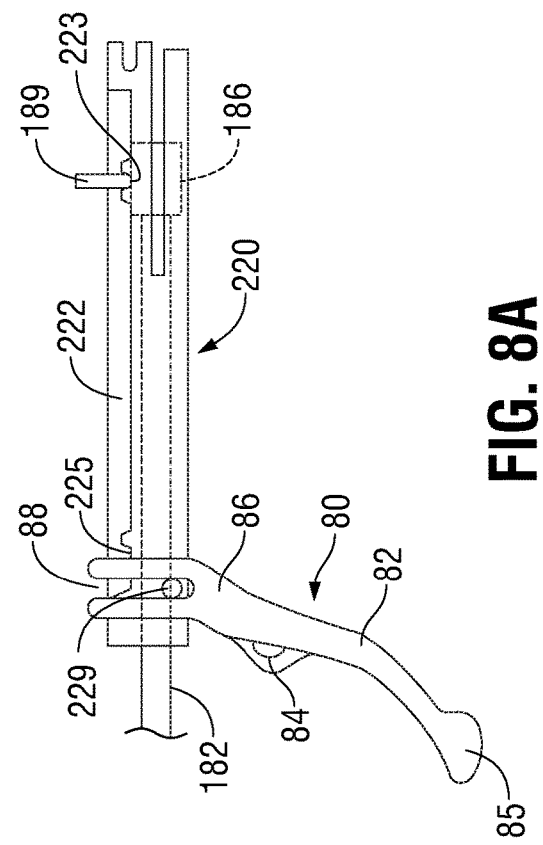
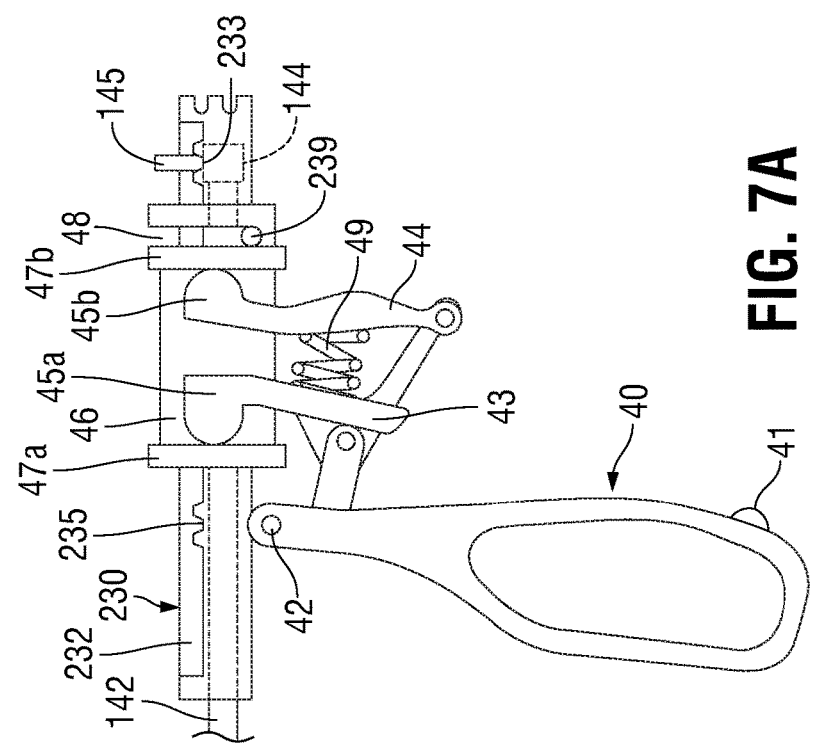

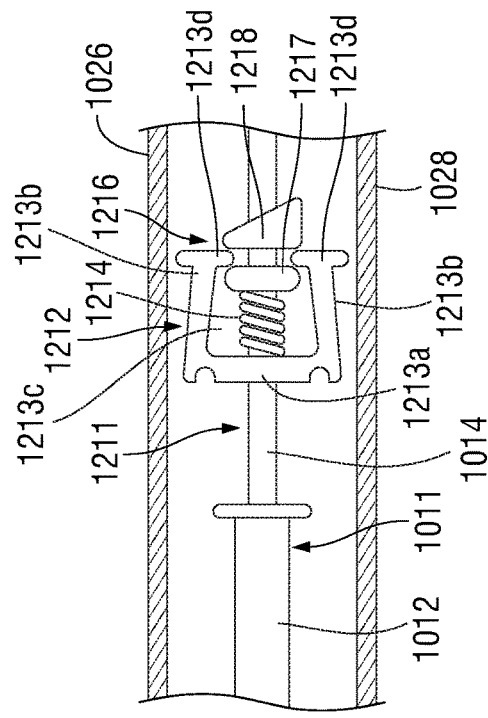
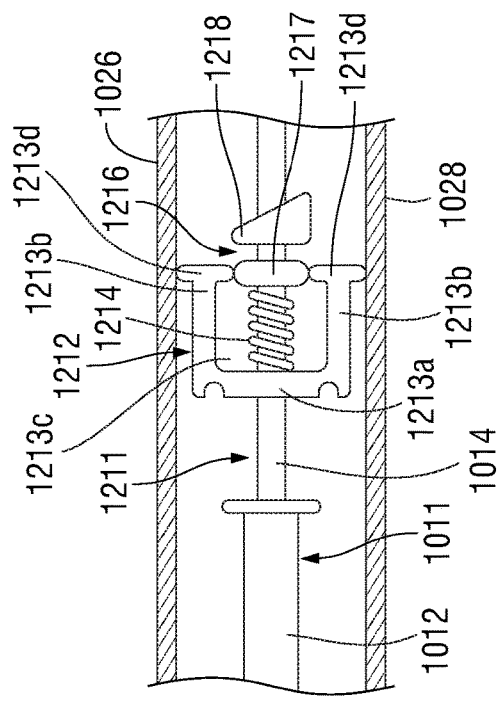
FIG. 17A
FIG. 17B
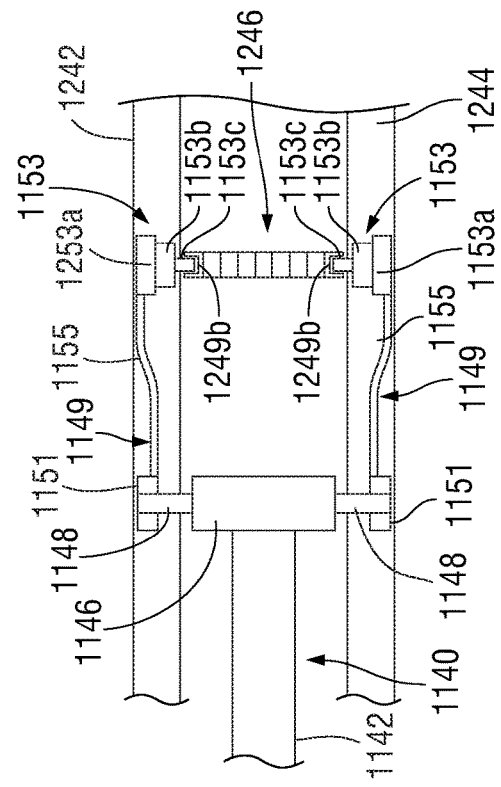
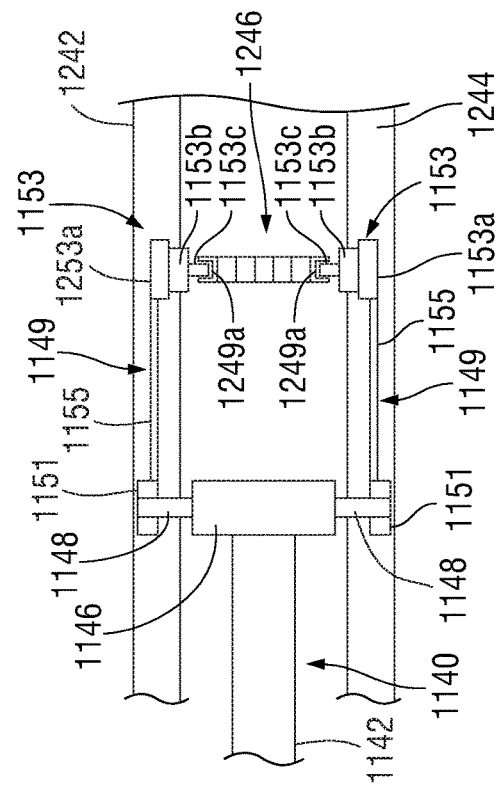
FIG. 18A
FIG. 18B

EXTENDABLE LENGTH SURGICAL INSTRUMENTS

CROSS REFERENCE TO RELATED APPLICATION

The present application is a U.S. National Stage Application under 35 U.S.C. § 371(a) of PCT/CN2014/087425 filed Sep. 25, 2014, the entire contents of which are incorporated by reference herein.

BACKGROUND

1. Technical Field

The present disclosure relates to medical devices. More particularly, the present disclosure relates to surgical instruments having extendable lengths to facilitate use in a variety of different surgical procedures and/or for a variety of different patient anatomies.

2. Discussion of Related Art

Electrosurgery involves the application of thermal and/or electrical energy to cut, dissect, ablate, coagulate, cauterize, seal, or otherwise treat biological tissue during a surgical procedure. Electrosurgery is typically performed using an electrosurgical generator operable to output energy and a handpiece including an end effector assembly adapted to transmit energy to tissue.

Electrosurgical forceps, for example, utilize mechanical action to constrict, grasp, treat, and/or dissect tissue. In particular, electrosurgical forceps utilize both mechanical clamping action and electrosurgical energy application to effect hemostasis by heating the tissue and blood vessels to treat tissue, e.g., cauterize, coagulate/desiccate, and/or seal tissue.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is a surgical instrument that generally includes a housing, a shaft coupled to and extending distally from the housing, an end effector assembly disposed at a distal end of the shaft, a movable handle coupled to the housing, a drive assembly coupled to the end effector assembly, and an extension mechanism disposed within the housing. The extension mechanism is configured to couple to the shaft and configured to couple between the movable handle and the drive assembly. The extension mechanism is further configured to move the shaft and drive assembly relative to the housing between a retracted position, wherein the shaft and drive assembly extend a first distance from the housing, and an extended position, wherein the shaft and drive assembly extend a second, different distance from the housing. The extension mechanism is coupled between the movable handle and the drive assembly in each of the retracted and extended positions such that the movable handle is operable to effect manipulation of the end effector assembly in each of the retracted and extended positions.

In an aspect of the present disclosure, the extension mechanism is further configured to incrementally move the shaft and drive assembly relative to the housing between a plurality of discrete intermediate positions disposed between the retracted position and the extended position. Alternatively, the extension mechanism may further be configured to continuously move the shaft and drive assembly relative to the housing between the retracted position, the extended position, and intermediate positions therebetween. In either configuration, the extension mechanism is coupled between the movable handle and the drive assembly in each of the intermediate positions such that the movable handle is operable to effect manipulation of the end effector assembly in each of the intermediate positions.

In another aspect of the present disclosure, the extension mechanism is transitionable between a use condition, wherein the shaft is retained in substantially fixed position relative to the housing and the drive assembly is coupled to the movable handle, and an extension/retraction condition, wherein the shaft is movable relative to the housing and the drive assembly is decoupled from the movable handle.

In yet another aspect of the present disclosure, the extension mechanism may further include an actuator translatable along the housing between a proximal position and a distal position for moving the shaft and drive assembly between the retracted position and the extended position.

In still another aspect of the present disclosure, the extension mechanism is configured such that, in each of the proximal and distal positions, the actuator is rotatable relative to the housing for transitioning the extension mechanism between the use condition and the extension/retraction condition.

In still yet another aspect of the present disclosure, the extension mechanism further includes a rotation knob that is selectively rotatable relative to the housing for transitioning the extension mechanism between the use condition and the extension/retraction condition.

In another aspect of the present disclosure, the extension mechanism further includes a rotatable actuator coupled to the shaft and the drive assembly. The rotatable actuator is selectively rotatable relative to the housing for moving the shaft and drive assembly between the retracted position and the extended position.

Another surgical instrument provided in accordance with aspects of the present disclosure generally includes a housing, a shaft coupled to and extending distally from the housing, an end effector assembly disposed at a distal end of the shaft, a knife blade disposed within the shaft, a movable handle coupled to the housing, a drive assembly, a trigger, a knife assembly coupled to the knife blade, and an extension mechanism. The end effector assembly includes first and second jaw members pivotable relative to one another between a spaced-apart position and an approximated position for grasping tissue therebetween. The knife blade is disposed within the shaft and is translatable relative to the shaft between a storage position, wherein the knife blade is positioned proximally of the first and second jaw members, and a deployed position, wherein the knife blade extends between the first and second jaw members for cutting tissue grasped therebetween. The drive assembly is coupled to one or both of the first and second jaw members of the end effector assembly. The extension mechanism is disposed within the housing and is configured to couple to the shaft, between the movable handle and the drive assembly, and between the trigger and the knife assembly. The extension mechanism is configured to move the shaft, drive assembly, and knife assembly relative to the housing between a retracted position, wherein the shaft, drive assembly, and knife assembly extend a first distance from the housing, and an extended position, wherein the shaft, drive assembly, and knife assembly extend a second, different distance from the housing. The extension mechanism is coupled between the movable handle and the drive assembly and between the trigger and the knife assembly in each of the retracted and extended positions such that the movable handle is operable to effect relative pivoting of the first and second jaw members of the end effector assembly in each of the retracted and extended positions, and such that the trigger is operable to effect translation of the knife blade in each of the retracted and extended positions.

In an aspect of the present disclosure, the extension mechanism is further configured to incrementally move the shaft, drive assembly, and knife assembly relative to the housing between a plurality of discrete intermediate positions disposed between the retracted position and the extended position. Alternatively, the extension mechanism may further be configured to continuously move the shaft, drive assembly, and knife assembly relative to the housing between the retracted position, the extended position, and intermediate positions therebetween. In either configuration, the extension mechanism is coupled between the movable handle and the drive assembly and between the trigger and the knife assembly in each of the intermediate positions such that the movable handle is operable to effect relative pivoting of the first and second jaw members of the end effector assembly in each of the intermediate positions, and such that the trigger is operable to effect translation of the knife blade in each of the intermediate positions.

In another aspect of the present disclosure, the extension mechanism is transitionable between a use condition, wherein the shaft is retained in substantially fixed position relative to the housing, the drive assembly is coupled to the movable handle via the extension mechanism, and the knife assembly is coupled to the trigger via the extension mechanism, and an extension/retraction condition, wherein the shaft is movable relative to the housing, the drive assembly is decoupled from the movable handle, and the knife assembly is decoupled from the trigger.

In still another aspect of the present disclosure, the extension mechanism further includes an actuator translatable along the housing between a proximal position and a distal position for moving the shaft, drive assembly, and knife assembly between the retracted position and the extended position.

In yet another aspect of the present disclosure, in each of the proximal and distal positions, the actuator is rotatable relative to the housing for transitioning the extension mechanism between the use condition and the extension/retraction condition.

In still yet another aspect of the present disclosure, the extension mechanism further includes a rotation knob that is selectively rotatable relative to the housing for transitioning the extension mechanism between the use condition and the extension/retraction condition.

In another aspect of the present disclosure, the extension mechanism further includes a rotatable actuator coupled to the shaft, drive assembly, and knife assembly. The rotatable actuator is selectively rotatable relative to the housing for moving the shaft, drive assembly, and knife assembly between the retracted position and the extended position.

In another aspect of the present disclosure, the first and second jaw members of the end effector assembly are adapted to connect to a source of energy for treating tissue grasped therebetween.

BRIEF DESCRIPTION OF THE DRAWINGS

Various aspects and features of the present disclosure are described herein with reference to the drawings wherein like reference numerals identify similar or identical elements:

FIG. 6A is a side view of the proximal portion of the shaft assembly of the forceps of FIG. 1 having the outer concentric tube member disposed thereabout in a proximal position;

FIG. 7A is a side view of the handle assembly and the proximal portion of the drive assembly of the forceps of FIG. 1 having the inner concentric tube member disposed thereabout in a proximal position;

FIG. 8A is a side view of the trigger assembly and the proximal portion of the knife assembly of the forceps of FIG. 1 having the middle concentric tube member disposed thereabout in a proximal position.

FIG. 17A is a longitudinal, cross-sectional view of the portion of the extension mechanism of the forceps of FIG. 12 dedicated to retaining the shaft, disposed in the first condition;

FIG. 17B is a longitudinal, cross-sectional view of the portion of the extension mechanism of the forceps of FIG. 12 dedicated to retaining the shaft, disposed in the second condition;

FIG. 18A is a longitudinal, cross-sectional view of the portion of the extension mechanism of the forceps of FIG. 12 dedicated to retaining the drive assembly, disposed in the first condition;

FIG. 18B is a longitudinal, cross-sectional view of the portion of the extension mechanism of the forceps of FIG. 12 dedicated to retaining the drive assembly, disposed in the second condition;

DETAILED DESCRIPTION

The various embodiments of the present disclosure detailed below with reference to FIGS. 1A-22 provide surgical instruments suitable for treating and/or cutting tissue. More specifically, the various embodiments of the present disclosure include surgical instruments having extendable length shafts, thus facilitating use in a variety of different surgical procedures and/or for a variety of different patient anatomies. Although the various embodiments of the present disclosure are detailed below with respect to endoscopic surgical forceps, the aspects and features of the present disclosure are equally applicable for use with any suitable surgical instrument for providing an extendable length shaft.

Figure 1A:
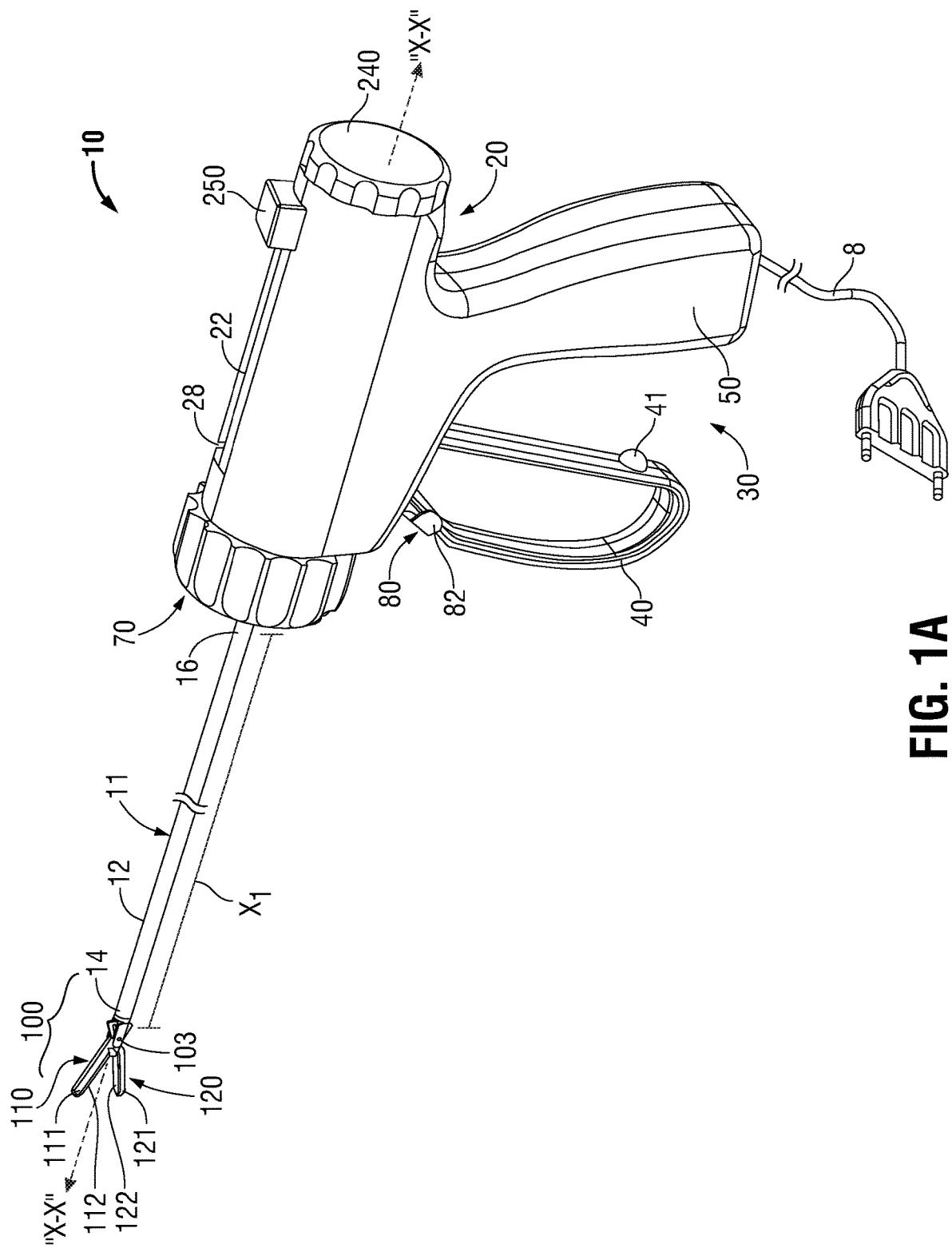
FIG. 1A is a perspective view of an endoscopic surgical forceps provided in accordance with the present disclosure, disposed in a retracted position defining a first shaft length.
Figure 1B:
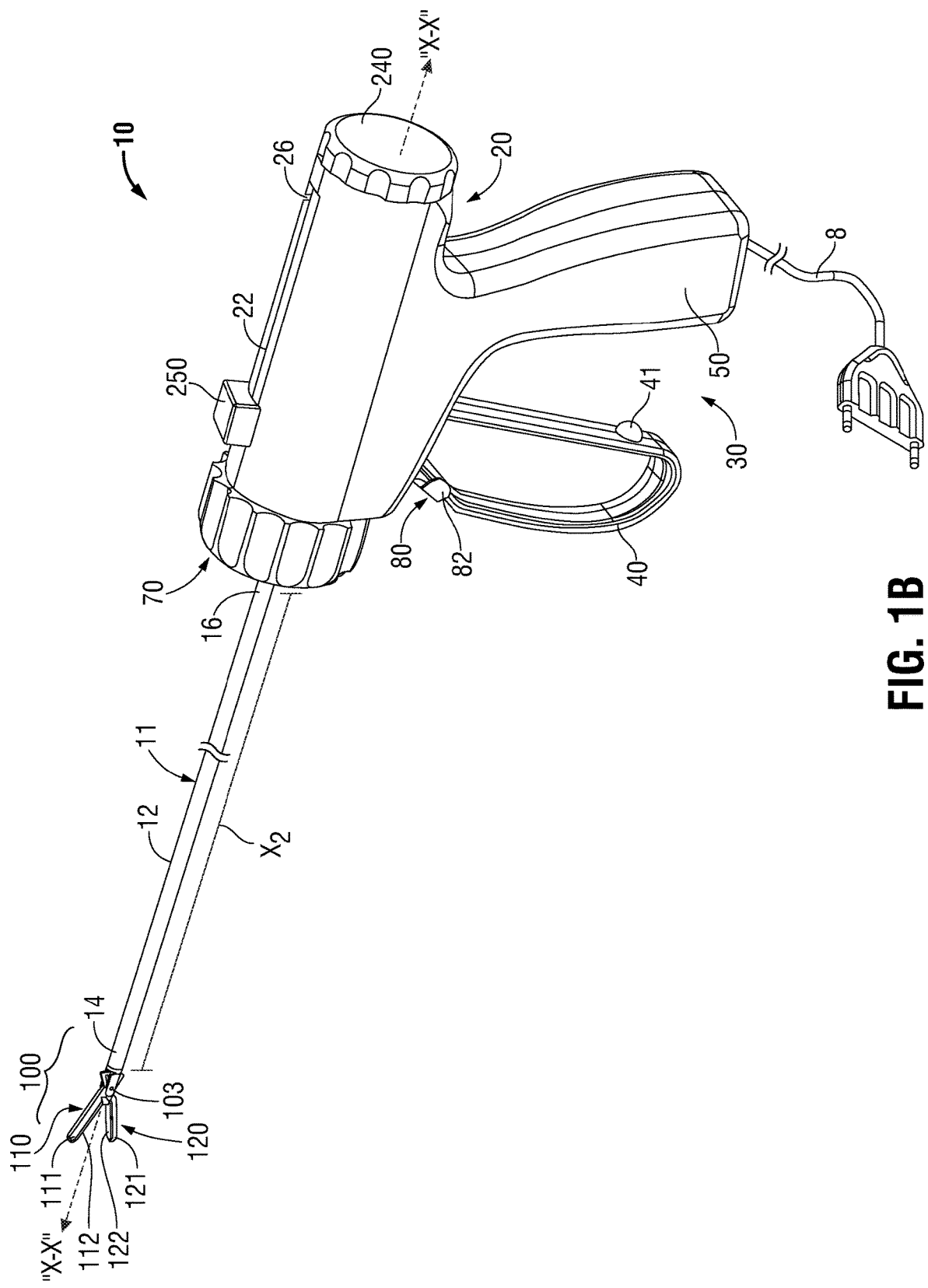
FIG. 1B is a perspective view of the forceps of FIG. 1A, disposed in an extended position defining a second shaft length.
Figure 2:
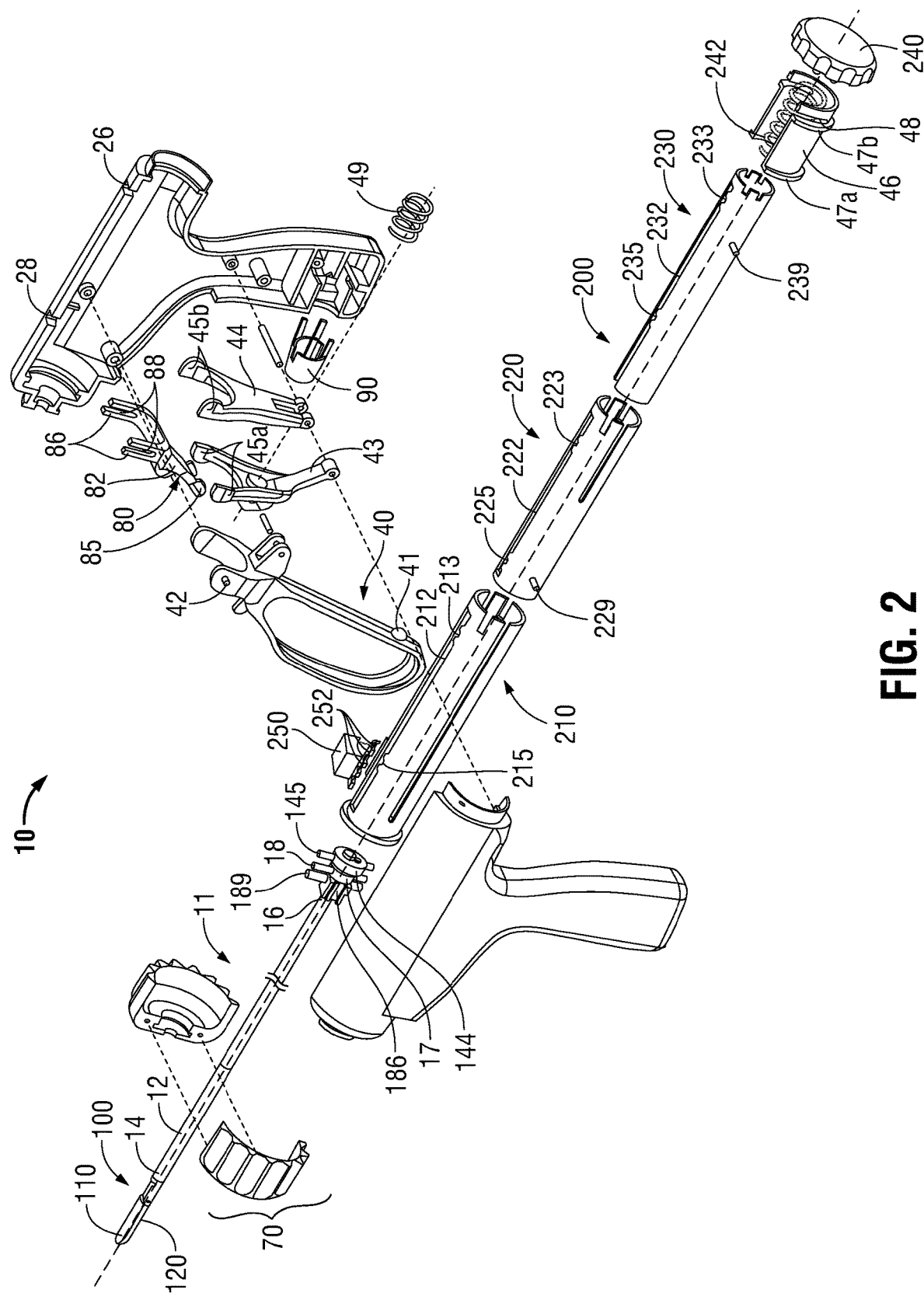
FIG. 2 is an exploded, perspective view of the forceps of FIG. 1.

Turning to FIGS. 1A-2, forceps 10 is provided defining a longitudinal axis "X-X" and generally including a housing 20, a handle assembly 30, a rotating assembly 70, a trigger assembly 80, an end effector assembly 100, and an extension mechanism 200. Housing 20 houses the internal working components of forceps 10. Handle assembly 30 includes a fixed handle 50 integrally associated with housing 20 and a movable handle 40 connected to a drive assembly 140 (FIG. 3) that, together, mechanically cooperate to impart movement of jaw members 110 and 120 of end effector assembly 100 between a spaced-apart position and an approximated position to grasp tissue therebetween. Rotating assembly 70 is rotatable in either direction about longitudinal axis "X-X" to rotate end effector assembly 100 about longitudinal axis "X-X." Trigger assembly 80 includes a trigger 82 that is operably coupled to a knife assembly 180 (FIG. 3) for selectively translating a knife blade 184 from a storage condition to a deployed condition wherein knife blade 184 extends through a knife channel (not explicitly shown) defined within one or both of jaw members 110, 120 of end effector assembly 100 to cut tissue disposed therebetween.

Forceps 10 further includes a shaft assembly 11 including a shaft 12 (see FIG. 3) having a distal end 14 configured to mechanically engage jaw members 110, 120 of end effector assembly 100 and a proximal end 16 that extends into housing 20. Forceps 10 also includes cable 8 that connects forceps 10 to an energy source (not shown), e.g., a generator or other suitable power source, although forceps 10 may alternatively be configured as a battery-powered device. Cable 8 includes a wire (or wires) (not shown) extending therethrough that has sufficient length to extend through shaft 12 in order to provide energy to at least one of tissue-contacting surfaces 112, 122 of jaw members 110, 120, respectively. An activation switch 90 (FIG. 2) is provided on housing 20 for selectively supplying energy to jaw members 110, 120 upon sufficient compression of movable handle 40, as detailed below.

Each of jaw members 110, 120 of end effector assembly 100 includes an outer insulative jaw housing 111, 121 and an electrically-conductive tissue-contacting surface 112, 122, respectively. Tissue-contacting surfaces 112, 122 are electrically coupled to activation switch 90 (FIG. 2) and the source of energy (not shown), e.g., via the wires (not shown) extending from cable 8 through forceps 10, such that energy may be selectively supplied to tissue-contacting surface 112 and/or tissue-contacting surface 122 and conducted therebetween and through tissue disposed between jaw members 110, 120 to treat tissue.

With additional reference to FIGS. 3-5B, extension mechanism 200 includes a set of concentric tube members, e.g., an outer tube member 210, a middle tube member 220, and an inner tube member 230. Outer tube member 210 is configured for operable coupling to shaft assembly 11 (see FIGS. 6A and 6B), middle tube member 220 is configured for operable coupling to knife assembly 180 and is operably coupled to trigger assembly 80 (see FIGS. 8A and 8B), and inner tube member 230 is configured for operable coupling to drive assembly 140 and is operably coupled to handle assembly 30 (see FIGS. 7A and 7B). More specifically, as will be described in greater detail below, shaft assembly 11, knife assembly 180, and drive assembly 140 are configured to operably couple to respective tube members 210, 220, 230 in each of a proximal position and a distal position relative to housing 20 and are configured to move in conjunction with one another between the respective proximal positions and the respective distal positions thereof to transition forceps 10 between a retracted position, wherein shaft 12 extends from housing 20 a first length "$X_1$," e.g., of about 37 cm (although other lengths are also contemplated), and an extended position, wherein shaft 12 extends from housing 20 a second length "$X_2$," e.g., of about 44 cm (although other lengths are also contemplated), that is greater than first length "$X_1$." Thus, as detailed below, forceps 10 is fully operational in both the retracted and extended positions.

Figure 3:
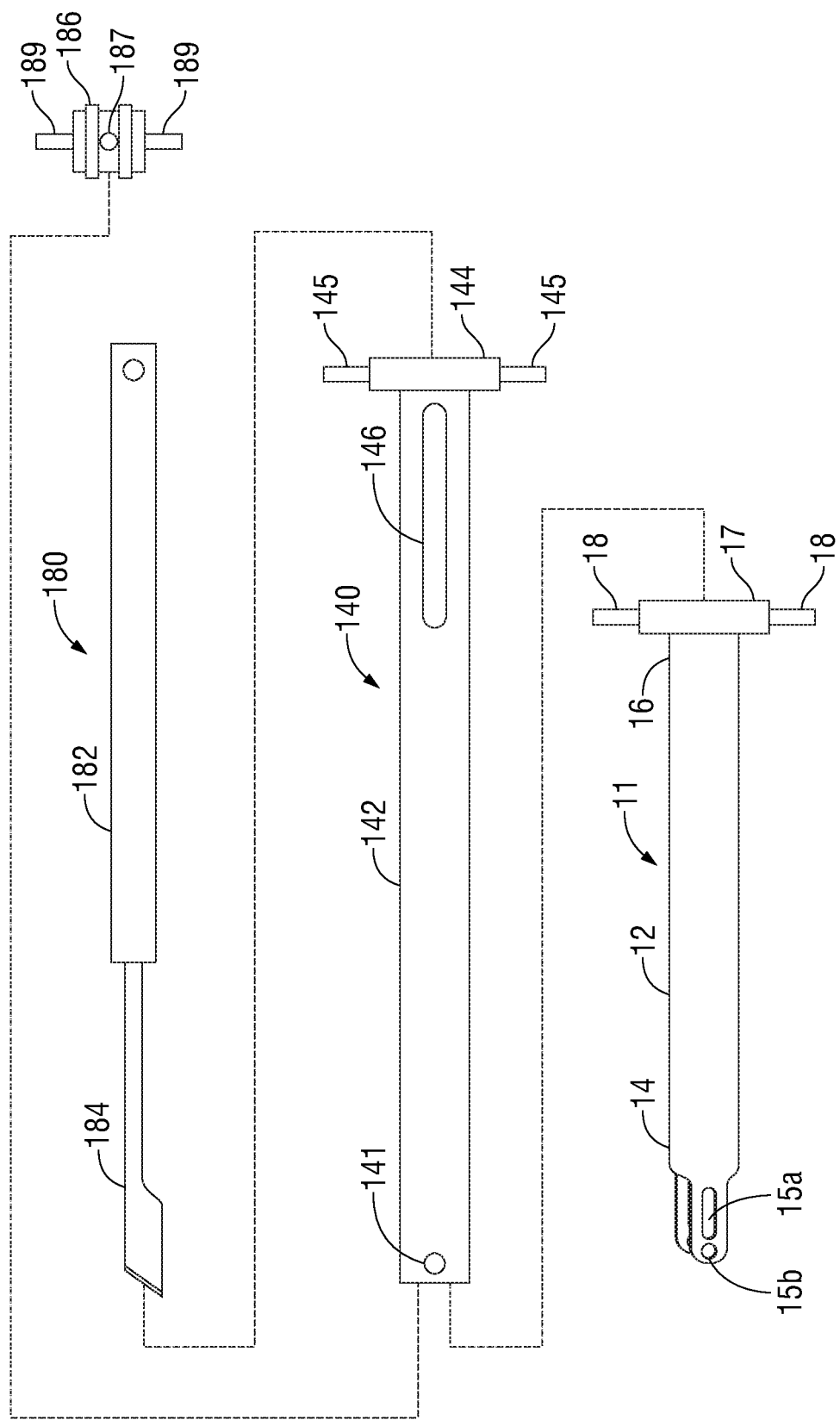
FIG. 3 is exploded, side view of the shaft, drive, and knife assemblies of the forceps of FIG. 1.

Referring to FIG. 3, in conjunction with FIG. 2, shaft assembly 11, drive assembly 140, and knife assembly 180 define a nested configuration wherein drive assembly 140 is slidably disposed within shaft assembly 11 and wherein knife assembly 180, in turn, is slidably disposed within drive assembly 140. Shaft assembly 11 includes shaft 12 and a collar 17 mounted to proximal end 16 of shaft 12. Collar 17 defines a pair of opposed posts 18 extending radially outwardly therefrom although in some embodiments only one post 18 or two or more posts 18 may be provided. Shaft 12 defines a bifurcated distal end 14 with each portion of the bifurcated distal end 14 defining a longitudinal slot 15a and an aperture 15b. Apertures 15b are configured to receive either end of a pivot pin 103 (FIG. 1A) that extends therebetween and through jaw members 110, 120 to pivotably couple jaw members 110, 120 to one another and shaft 12. Longitudinal slots 15a are configured to receive either end of a drive pin 141 of drive assembly 140 that also extends through oppositely angled slots (not explicitly shown) of jaw members 110, 120 to guide translation of drive pin 141 through those slots to effect pivoting of jaw members 110, 120 relative to one another between the spaced-apart and approximated positions.

Drive assembly 140 includes a drive bar 142 having drive pin 141 extending transversely therethrough towards the distal end of drive bar 142. Drive assembly 140 further includes a proximal collar 144 that, similarly as with collar 17 of shaft assembly 11, defines a pair of opposed posts 145 extending radially outwardly therefrom although in some embodiments only one post 145 or two or more posts 145 may alternatively be provided. Drive assembly 140 is selectively translatable through shaft 11 and relative to end effector assembly 100 to effect pivoting of jaw members 110, 120 relative to one another between the spaced-apart and approximated positions. Drive bar 142 further defines opposed proximal slots 146 defined therethrough towards the proximal end thereof. Opposed proximal slots 146 permit coupling of knife collar 186 with knife drive bar 182, as detailed below. Drive bar 142 defines a length greater than that of shaft 11 such that, despite drive bar 142 being slidably disposed within shaft 11, a proximal portion of drive bar 142, e.g., the portion including proximal slots 146 and proximal collar 144, remains proximally of shaft 12.

Knife assembly 180 includes knife drive bar 182, knife blade 184, and knife collar 186. Knife blade 184 extends distally from knife drive bar 182. Knife collar 186 is slidably disposed about drive bar 142 and is coupled to the proximal end of knife drive bar 182 via pin 187 which extends through proximal slots 146 of proximal collar 144 of drive assembly 140 to permit longitudinal translation of knife assembly 180 through and relative to drive bar 142 of drive assembly 140. Knife collar 186, similarly as with collar 17 of shaft assembly 11, defines a pair of opposed posts 189 extending radially outwardly therefrom although in some embodiments only one post 189 or two or more posts 189 may alternatively be provided.

Figure 4:
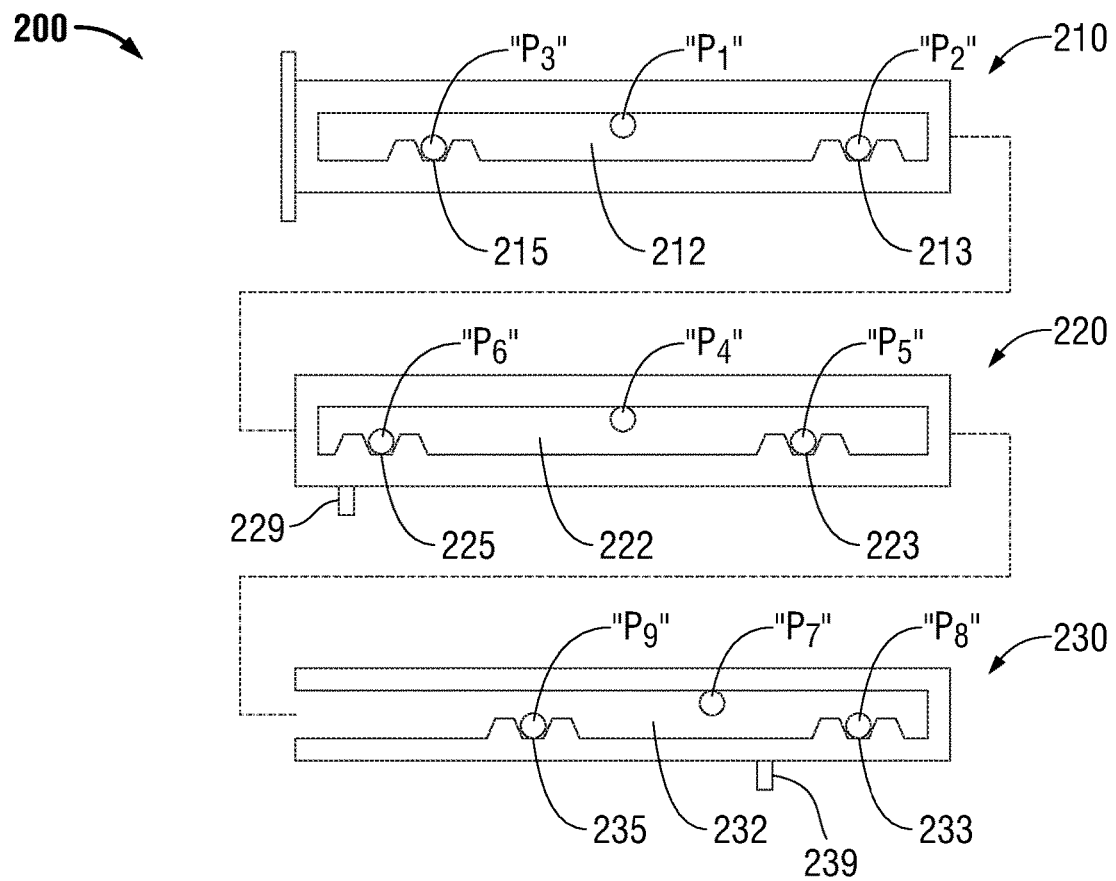
FIG. 4 is an exploded, top schematic illustration of the outer, middle, and inner concentric tube members of the forceps of FIG. 1.
Figures 5A, 5B:
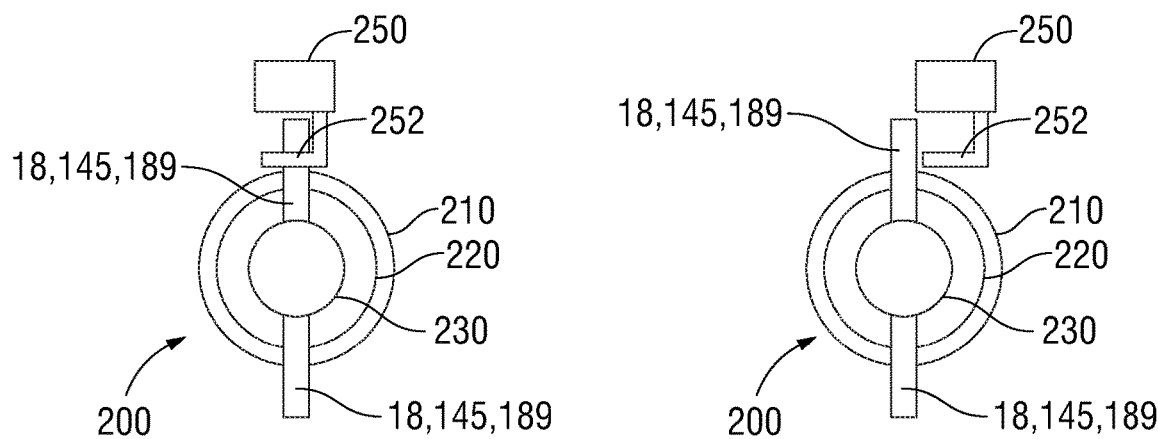
FIG. 5A is a transverse, cross-sectional view of the shaft, drive, and knife assemblies of the forceps of FIG. 1 with the actuator disposed in a first condition.
FIG. 5B is a transverse, cross-sectional view of the shaft, drive, and knife assemblies of the forceps of FIG. 1 with the actuator disposed in a second condition.

Turning to FIGS. 4 and 5A-5B, in conjunction with FIGS. 2 and 3, as noted above, outer tube member 210 is configured to operably couple to shaft assembly 11 in each of the proximal and distal positions of shaft assembly 11, middle tube member 220 is configured to operably couple to knife assembly 180 in each of the proximal and distal positions of knife assembly 180, and inner tube member 230 is configured to operably couple to drive assembly 140 in each of the proximal and distal positions of drive assembly 140. To enable such a configuration, each tube member 210, 220, 230 defines a pair of opposed longitudinally-extending engagement slots 212, 222, 232, each defining a proximal engagement notch 213, 223, 233 and a distal engagement notch 215, 225, 235, respectively. Posts 18 of collar 17 of shaft assembly 11 are slidable through slots 212 of tube member 210 (see, e.g., position "$P_1$" of posts 18) and are configured for releasable engagement within proximal and distal engagement notches 213, 215, respectively, thereof (see, e.g., positions "$P_2$" and "$P_3$," respectively, of posts 18). Posts 189 of knife collar 186 of knife assembly 180 are slidable through slots 222 of tube member 220 (see, e.g., position "$P_4$" of posts 189) and are configured for releasable engagement within proximal and distal engagement notches 223, 225, respectively, thereof (see, e.g., positions "$P_5$" and "$P_6$," respectively, of posts 189). Posts 145 of proximal collar 144 of drive assembly 140 are slidable through slots 232 of tube member 230 (see, e.g., position "$P_7$" of posts 145) and are configured for releasable engagement within proximal and distal engagement notches 233, 235, respectively, thereof (see, e.g., positions "$P_8$" and "$P_9$," respectively, of posts 145).

Referring again to FIGS. 2-5B, extension mechanism 200 further includes a rotation knob 240 extending proximally from housing 20, and an actuator 250 that extends upwardly through a slot 22 defined within housing 20 to be externally accessible. Rotation knob 240 is coupled to tube members 210, 220, 230 and actuator 250 and is rotatable about longitudinal axis "X-X" relative to housing 20 to similarly rotate tube members 210, 220, 230 and actuator 250 relative to housing 20 and the internal assemblies thereof, e.g., shaft assembly 11, knife assembly 180, and drive assembly 140, between an extension/retraction condition (FIG. 5A) and a use condition (FIG. 5B). A torsion biasing member 242 is provided to bias rotation knob 240 and, thus, actuator 250, towards the use condition of (FIG. 5B) extension mechanism 200, although other configurations are also contemplated.

In the extension/retraction condition of extension mechanism 200, actuator 250 is positioned such that posts 18, 145, and 189 of shaft assembly 11, drive assembly 140, and knife assembly 180, respectively, are engaged between spaced-apart fingers 252 of actuator 250 (FIG. 5A) and such that actuator 250 is disposed in the body portion of longitudinal slot 22 of housing 20. Further, in the extension/retraction condition, tube members 210, 220, 230 are oriented relative to posts 18, 189, and 145 such that posts 18, 189, and 145 are spaced-apart from proximal engagement notch 213, 223, 233 (where shaft assembly 11, drive assembly 140, and knife assembly 180 are disposed in their respective proximal positions) or distal engagement notch 215, 225, 235 (where shaft assembly 11, drive assembly 140, and knife assembly 180 are disposed in their respective distal positions). Thus, in the extension/retraction condition, actuator 250 may be translated through the body portion of slot 22 and relative to housing 20 to cooperatively move shaft assembly 11, drive assembly 140, and knife assembly 180 relative to tube members 210, 220, 230 between their respective proximal and distal positions to transition forceps 10 between the retracted and extended positions. Once the desired position, e.g., the retracted position or the extended position, has been achieved, extension mechanism 200 may be transitioned to the use condition, as detailed below.

In order to transition extension mechanism 200 to the use condition, with forceps 10 disposed in the retracted position or the extended position, rotation knob 240 is rotated in the opposite direction to effect rotation of spaced-apart fingers 252 of actuator 250 out of engagement with posts 18, 145, and 189, rotation of actuator 250 into engagement with the proximal or distal catch 26, 28 of longitudinal slot 22 (FIGS. 1A and 1B, respectively), and rotation of tube members 210, 220, 230 into position such that posts 18, 189, and 145 are engaged within proximal engagement notches 213, 223, 233 (where shaft assembly 11, knife assembly 180, and drive assembly 140 are disposed in their respective proximal positions) or distal engagement notches 215, 225, 235 (where shaft assembly 11, knife assembly 180, and drive assembly 140 are disposed in their respective distal positions).

With extension mechanism 200 disposed in the use condition and forceps 10 disposed in the retracted position, shaft assembly 11, knife assembly 180, and drive assembly 140 are disposed in their respective proximal positions wherein posts 18 of collar 17 of shaft assembly 11 are engaged within proximal engagement notches 213 at position "P$_2$," posts 189 of knife collar 186 of knife assembly 180 engaged within proximal engagement notches 223 at position "P$_5$," and posts 145 of proximal collar 144 of drive assembly 140 are engaged within proximal engagement notches 233 at position "P$_8$." On the other hand, with extension mechanism 200 disposed in the use condition and forceps 10 disposed in the extended position, shaft assembly 11, knife assembly 180, and drive assembly 140 are disposed in their respective distal positions wherein posts 18 of collar 17 of shaft assembly 11 are engaged within distal engagement notches 215 at position "P$_3$," posts 189 of knife collar 186 of knife assembly 180 engaged within distal engagement notches 225 at position "P$_6$," and posts 145 of proximal collar 144 of drive assembly 140 are engaged within distal engagement notches 235 at position "P$_9$." As detailed below, with drive assembly 140 and knife assembly 180 operably coupled to their respective tube member 230, 220 in both the retracted and extended positions, handle assembly 30, which is coupled to tube member 230, may be manipulated to effect pivoting of jaw members 110, 120 between the spaced-apart and approximated positions, and trigger assembly 80, which is coupled to tube member 220, may be manipulated to translate knife blade 184 between the storage and deployed positions. Further, as also detailed below, with extension mechanism 200 disposed in the use condition, shaft assembly 11 is retained in fixed longitudinal position relative to housing 20 in both the retracted and extended positions of shaft assembly 11.

Figure 6B:
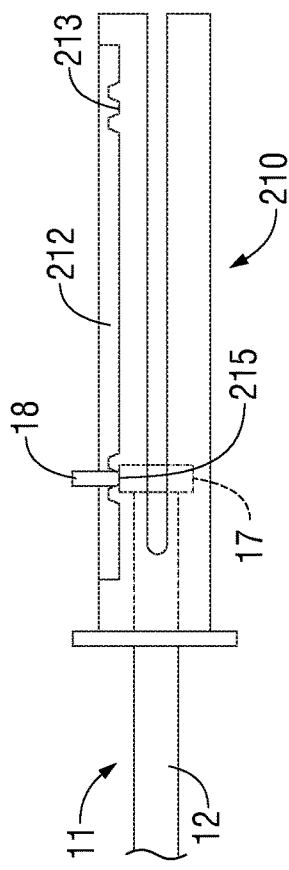
FIG. 6B is a side view of the proximal portion of the shaft assembly of the forceps of FIG. 1 having the outer concentric tube member disposed thereabout in a distal position.

Referring to FIGS. 6A and 6B, in conjunction with FIG. 2, in the retracted position (FIG. 6A) of forceps 10, shaft assembly 11 is engaged with tube member 210, e.g., posts 18 of collar 17 of shaft assembly 11 are engaged within proximal engagement notches 213 of tube member 210. As such, in this position, since tube member 210 is secured in fixed longitudinal position relative to housing 20, shaft assembly 11 is likewise secured in fixed longitudinal position relative to housing 20. Similarly, in the extended position (FIG. 6B) of forceps 10, shaft assembly 11 is engaged with tube member 210, e.g., posts 18 of collar 17 of shaft assembly 11 are engaged within distal engagement notches 215 of tube member 210. As such, in this position, since tube member 210 is secured in fixed longitudinal position relative to housing 20, shaft assembly 11 is likewise secured in fixed longitudinal position relative to housing 20.

Figure 7B:
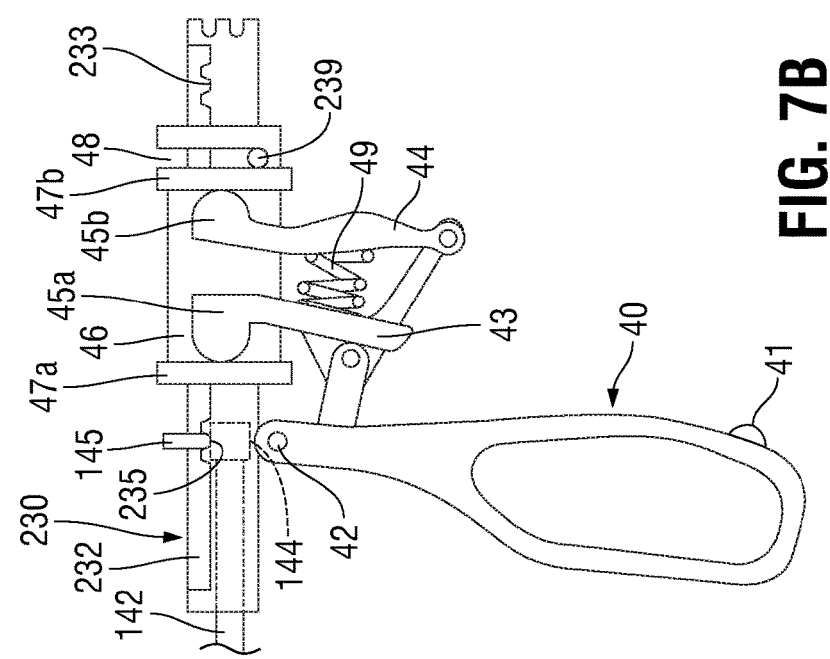
FIG. 7B is a side view of the handle assembly and the proximal portion of the drive assembly of the forceps of FIG. 1 having the inner concentric tube member disposed thereabout in a distal position.
Figure 9A:
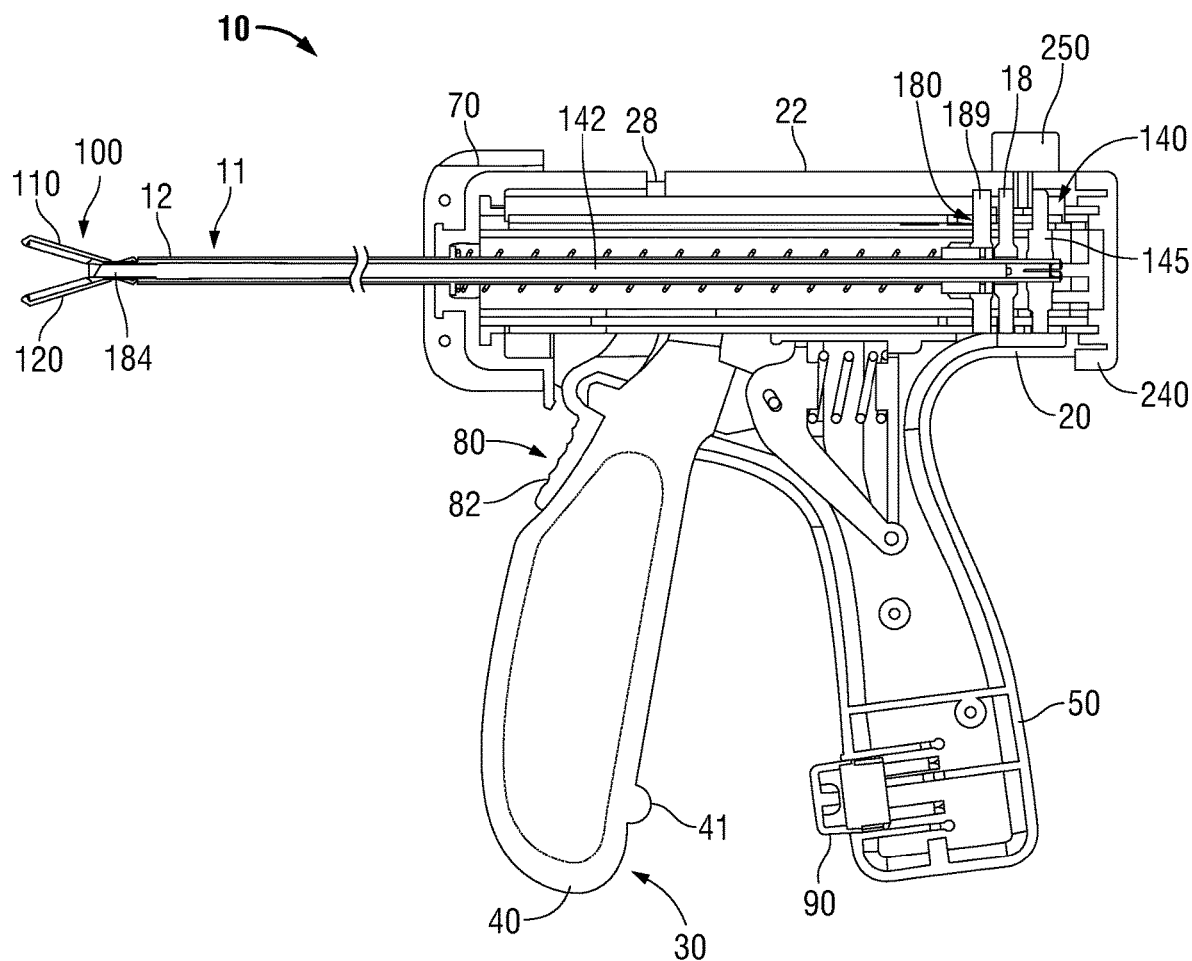
FIG. 9A is a longitudinal, cross-sectional view of the forceps of FIG. 1 disposed in a retracted position.
Figure 9B:
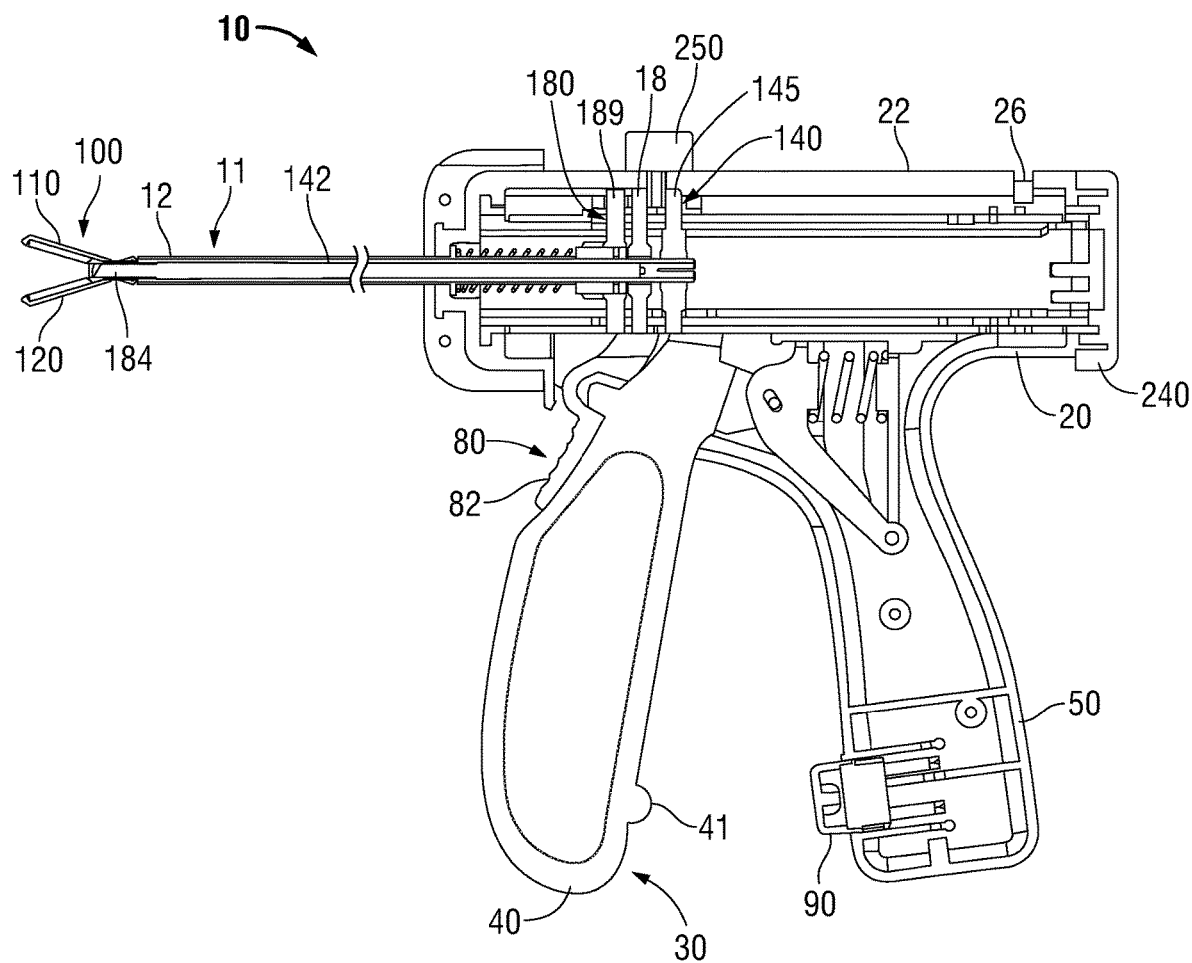
FIG. 9B is a longitudinal, cross-sectional view of the forceps of FIG. 1 disposed in an extended position.

Referring to FIGS. 7A and 7B, in conjunction with FIG. 2, as mentioned above, handle assembly 30 and, more specifically, movable handle 40, is coupled to tube member 230 such that, when drive assembly 140 is also coupled to tube member 230, movable handle 40 may be manipulated relative to fixed handle 50 to translate drive bar 142 through shaft 12 to effect pivoting of jaw members 110, 120 between the spaced-apart and approximated positions. Movable handle 40 is pivotably coupled to housing 20 (FIG. 2) via a split pivot 42. A pair of pivotably-coupled linkages 43, 44 is coupled between movable handle 40 and arms 45a, 45b. Linkages 43, 44 and arms 45a, 45b define bifurcated configurations for positioning on either side of tube member 230. A sleeve 46 is disposed about tube member 230 with arms 45a, 45b retained between raised portions 47a, 47b of sleeve 46 on either side of tube member 230 and sleeve 46. Sleeve 46 is coupled to tube member 230 via receipt of pin 239 of tube member 230 within slot 48 defined within sleeve 46, thus longitudinally securing sleeve 46 and tube member 230 to one another but permitting relative rotation therebetween, e.g., such that extension mechanism 200 may be transitioned between the use condition and the extension/retraction condition. A biasing member 49 disposed between arms 45a, 45b is provided to bias movable handle 40 towards an initial position, corresponding to the spaced-apart position of jaw members 110, 120, although other configurations are also contemplated.

Regardless of whether drive assembly 140 is coupled to tube member 230 in the proximal position (FIG. 7A) or the distal position (FIG. 7B), pivoting of movable handle 40 about pivot 42 and towards fixed handle 50 urges arms 45a, 45b proximally which, in turn, urge sleeve 46, tube member 230 and, ultimately, drive bar 142 proximally to pivot jaw members 110, 120 towards the approximated position. On the other hand, release or return of movable handle 40 away from fixed handle 50 urges arms 45a, 45b distally which, in turn, urges sleeve 46, tube member 230 and, ultimately, drive bar 142 distally to pivot jaw members 110, 120 towards the spaced-apart position.

Figure 8B:
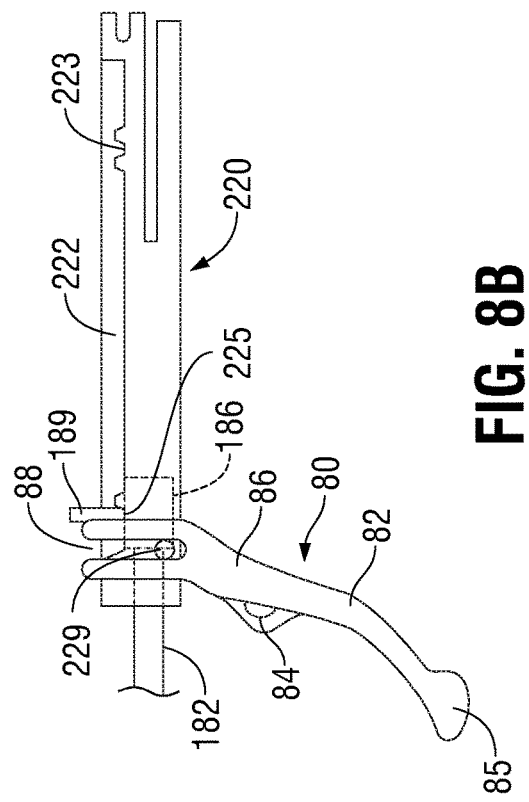
FIG. 8B is a side view of the trigger assembly and the proximal portion of the knife assembly of the forceps of FIG. 1 having the middle concentric tube member disposed thereabout in a distal position.

Referring to FIGS. 8A and 8B, in conjunction with FIG. 2, as mentioned above, trigger assembly 80 is coupled to tube member 220 such that, when knife assembly 180 is also coupled to tube member 220, trigger 82 of trigger assembly 80 may be manipulated relative to housing 20 to translate knife drive bar 182 through shaft 12 and relative to end effector assembly 100 to translate knife blade 184 between the storage and deployed positions. Trigger 82 is pivotably coupled to housing 20 (FIG. 2) via a pivot 84 at an intermediate portion of trigger 82. A toggle member 85 extends downwardly from the intermediate portion of trigger 82, while a pair of spaced-apart legs 86 extends upwardly from the intermediate portion of trigger 82. Legs 86 are configured for positioning on either side of tube member 220 and each defines a slot 88 configured to receive pin 229 of tube member 220 to longitudinally secure trigger assembly 80 and tube member 220 to one another but still permit relative rotation therebetween, e.g., such that extension mechanism 200 may be transitioned between the use condition and the extension/retraction condition. A biasing member (not explicitly shown) may be provided to bias trigger 82 such that knife blade 184 is based towards the storage position, although other configurations are also contemplated.

Regardless of whether knife assembly 180 is coupled to tube member 220 in the proximal position (FIG. 8A) or the distal position (FIG. 8B), actuating toggle member 85 rotates trigger 82 about pivot 84 to thereby urge legs 86 distally which, in turn, urges tube member 220 and, ultimately, knife drive bar 182 distally to advance knife blade 184 from the storage condition towards the deployed condition to cut tissue grasped between jaw members 110, 120. On the other hand, release or return of trigger 82 urges tube member 220 proximally and, ultimately, knife drive bar 182 proximally to return knife blade 184 to the storage position.

With reference to FIGS. 9A-11, the use and operation of forceps 10 is described. Initially, referring to FIGS. 9A and 9B, it is determined whether use of forceps 10 in the retracted position (FIG. 9A) or the extended position (FIG. 9B) is desired. In order to transition forceps 10 between the retracted position (FIG. 9A) and the extended position (FIG. 9B), rotation knob 240 is rotated in a first direction to transition extension mechanism 200 from the use condition to the extension/retraction condition. Thereafter, actuator 250 may be translated through slot 22 and relative to housing 20 to move forceps 10 between the retracted position (FIG. 9A) and the extended position (FIG. 9B). Once the desired position has been achieved, e.g., the extended position (FIG. 9B), rotation knob 240 is rotated in a second, opposite direction to transition extension mechanism 200 from the extension/retraction condition back to the use condition. Once returned to the use condition, forceps 10 is ready for use. The use and operation of forceps 10 is detailed below with respect to forceps 10 being disposed in the extended position. The use and operation of forceps 10 in the retracted position is similar and, thus, not detailed herein for purposes of brevity.

Figure 10:
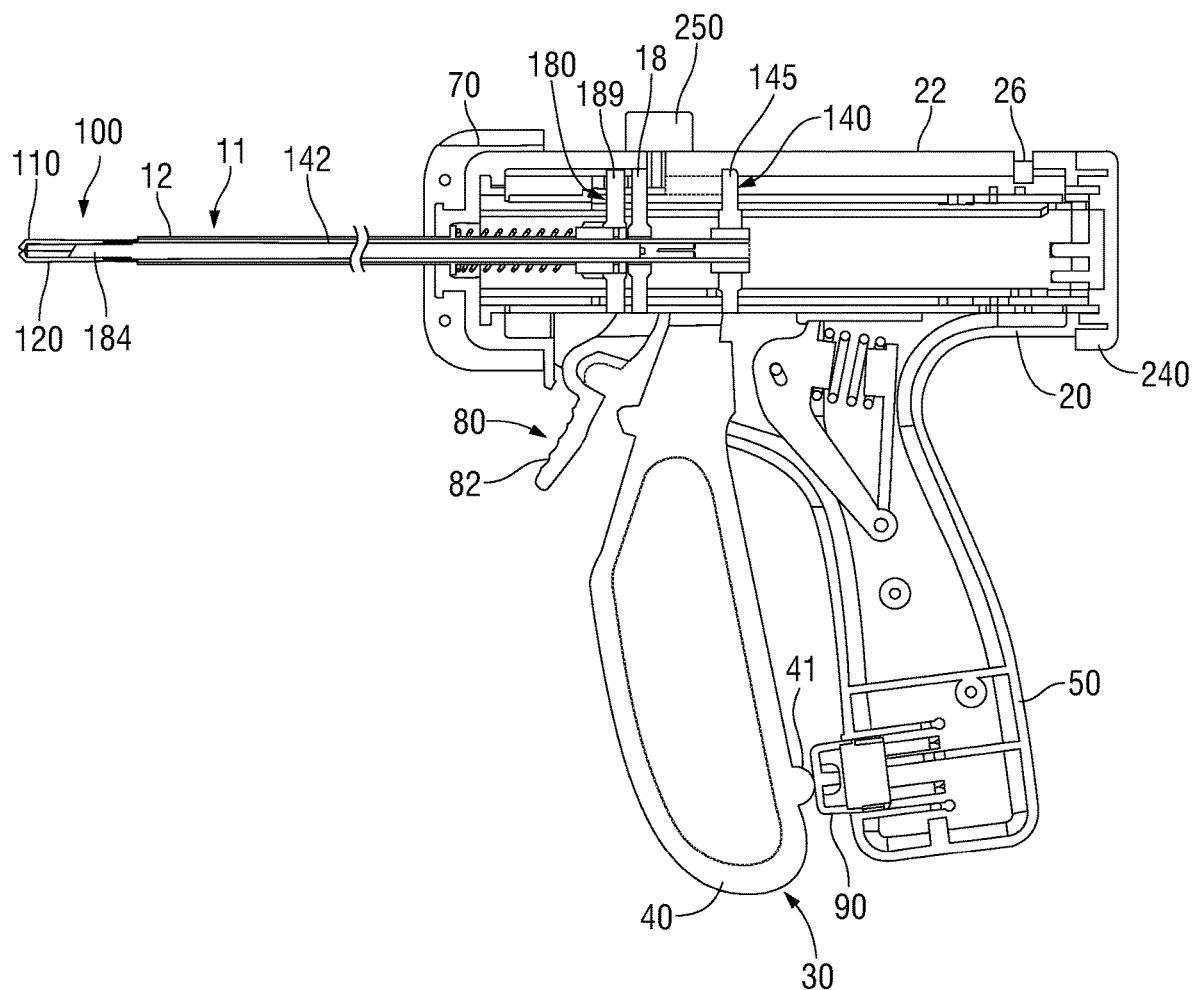
FIG. 10 is a longitudinal, cross-sectional view of the forceps of FIG. 1 disposed in the extended position with the jaw members disposed in an approximated position.
Figure 11:
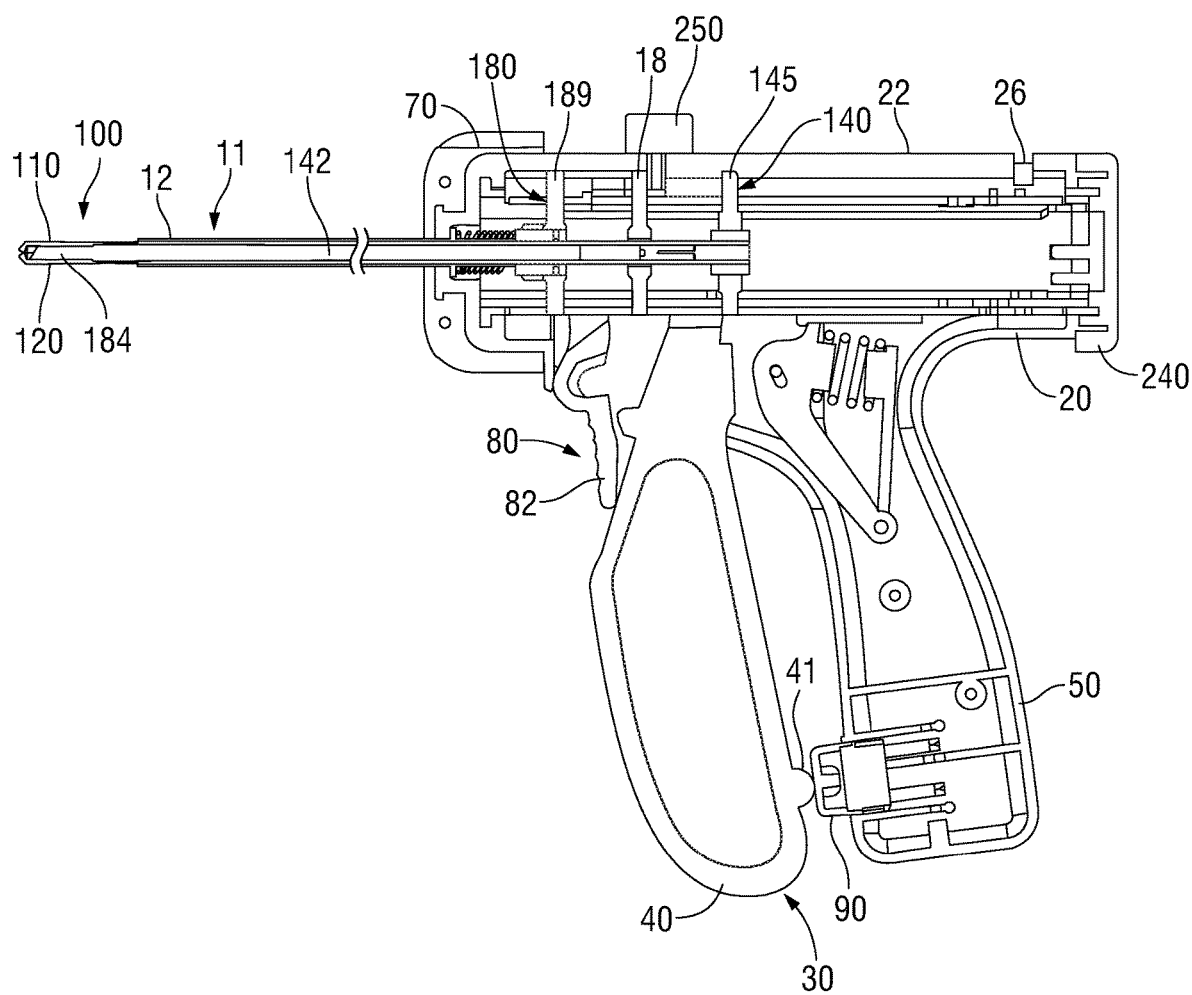
FIG. 11 is a longitudinal, cross-sectional view of the forceps of FIG. 1 disposed in the extended position with the jaw members disposed in an approximated position and the knife disposed in a deployed position.

Referring to FIGS. 9B-11, the use and operation of forceps 10, e.g., for grasping, treating, and/or cutting tissue, is described. With jaw members 110, 120 disposed in the spaced-apart position (FIG. 9B), end effector assembly 100 may be maneuvered into position such that tissue to be grasped, treated, and/or cut, is disposed between jaw members 110, 120. Next, movable handle 40 is depressed, or pulled proximally relative to fixed handle 50 such that jaw members 110, 120 are pivoted relative to one another from the spaced-apart position to the approximated position to grasp tissue therebetween (FIG. 10). Upon further depression of movable handle 40, protrusion 41 of movable handle is urged into contact with activation switch 90 (FIG. 2) sufficiently so as to activate activation switch 90 (FIG. 2) which initiates the supply of energy to jaw members 110, 120. More specifically, energy may be supplied to surface 112 of jaw member 110 and/or surface 122 of jaw member 120 and conducted through tissue to treat tissue, e.g., to effect a tissue seal or otherwise treat tissue. Once tissue treatment is complete (or to cut untreated tissue), trigger 82 is actuated to deploy knife blade 184 (FIG. 11) from within shaft 12 to between jaw members 110, 120 to cut tissue grasped between jaw members 110, 120. When tissue cutting is complete, trigger 82 may be released to return knife blade 184 to the retracted position. Thereafter, movable handle 40 may be released or returned to its initial position such that jaw members 110, 120 are moved back to the spaced-apart position (FIG. 9B) to release the treated and/or divided tissue.

Turning now to FIGS. 12-18B, another embodiment of a forceps 1010 provided in accordance with the present disclosure is shown. Similar to forceps 10 (FIGS. 1A-11), forceps 1010 is transitionable between and operable in each of a retracted position and an extended position. Further, forceps 1010 is transitionable between an operable in a plurality of discrete intermediate positions between the retracted and extended positions. For example, the retracted position may correspond to a shaft length of about 37 cm (although other lengths are also contemplated), the extended position may correspond to a shaft length of about 44 cm (although other lengths are also contemplated), and the intermediate positions may define a step size of about 0.25 cm (although other constant or varied steps sizes are also contemplated). For purposes of brevity, only the differences between forceps 1010 and forceps 10 (FIGS. 1A-11) will be described in detail below, while similarities will only be summarily described or omitted entirely.

Figure 12:
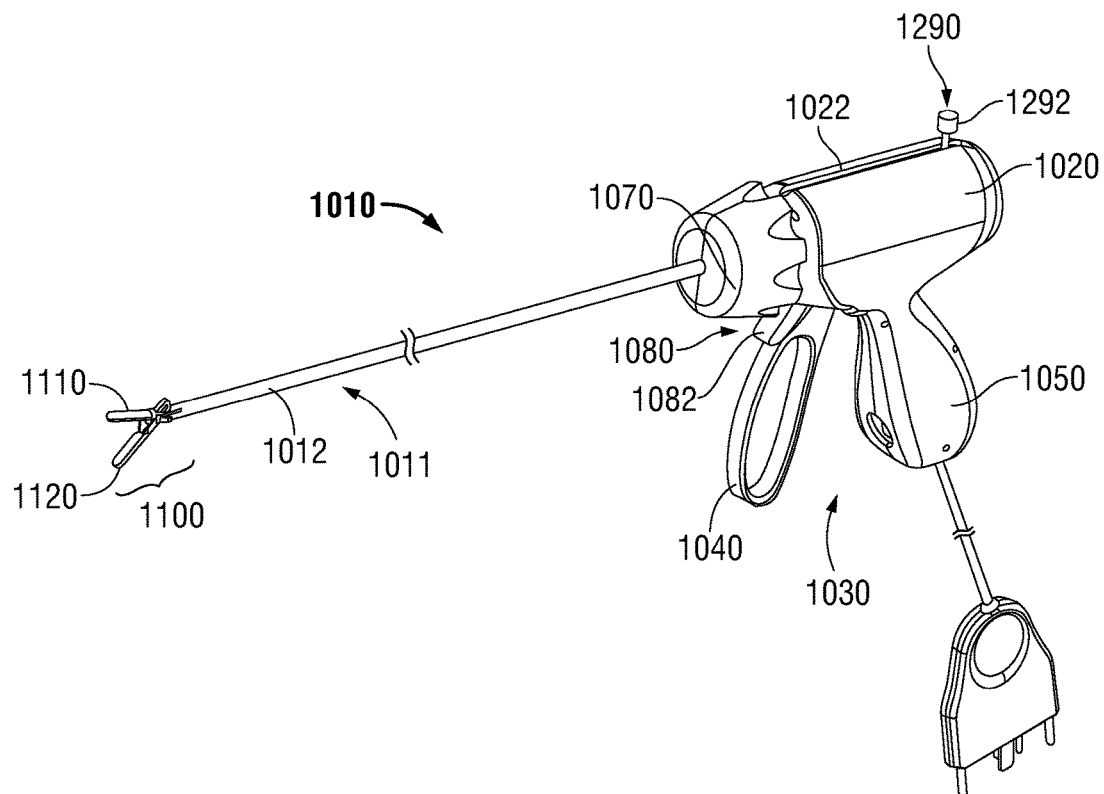
FIG. 12 is a perspective view of another endoscopic surgical forceps provided in accordance with the present disclosure.
Figure 13:
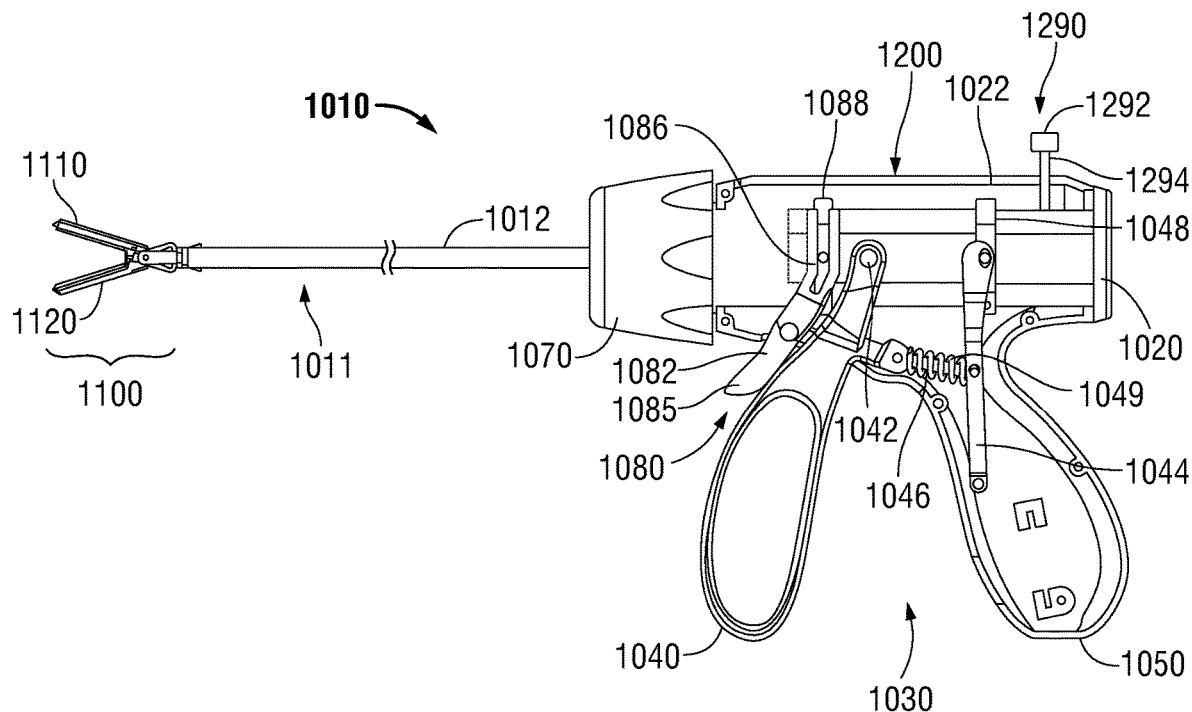
FIG. 13 is a side view of the forceps of FIG. 12 with portions of the housing removed to illustrate the internal components of the forceps.
Figure 14:
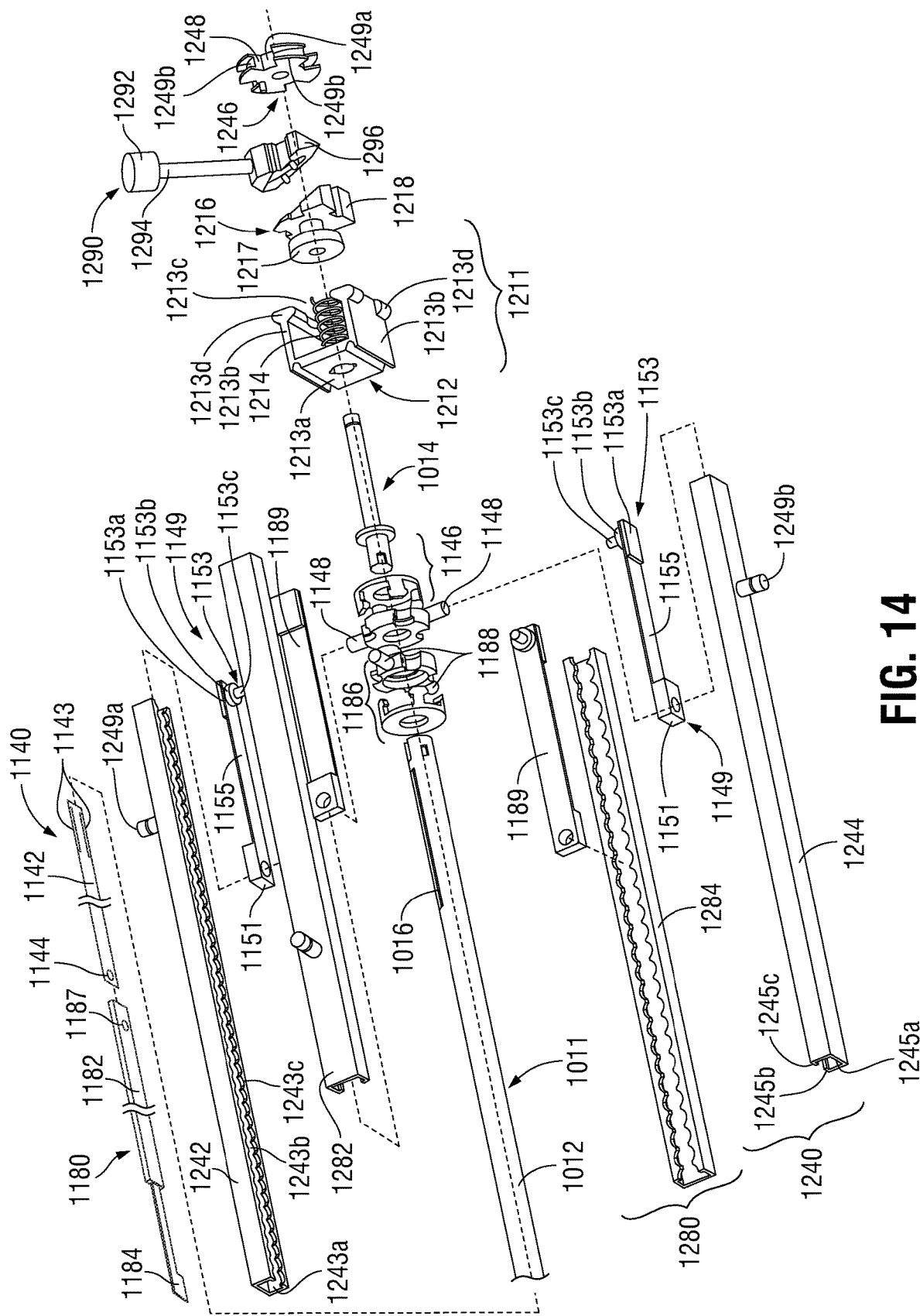
FIG. 14 is an exploded, perspective view of the internal operating components of the forceps of FIG. 12.
Figure 15:
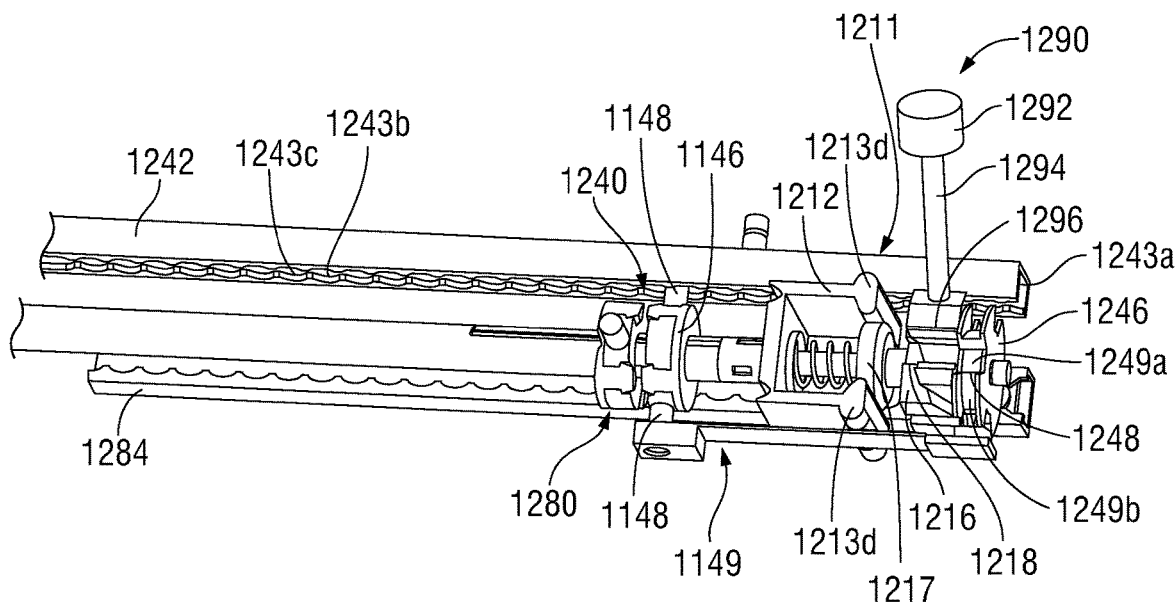
FIG. 15 is a side, perspective view of the extension mechanism of the forceps of FIG. 12, disposed in a first condition.
Figure 16:
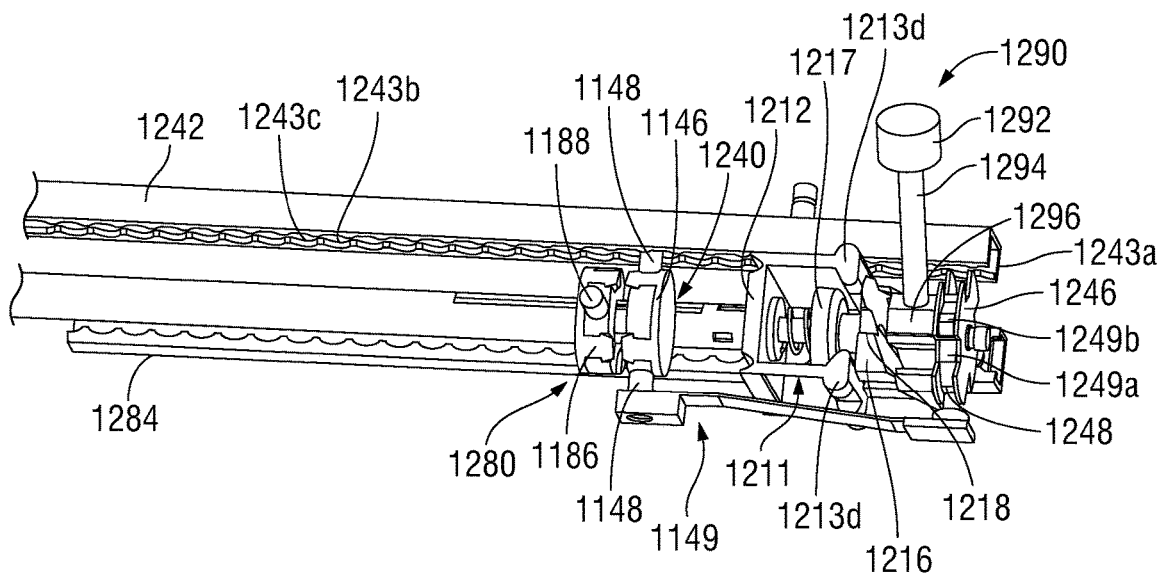
FIG. 16 is a side, perspective view of the extension mechanism of the forceps of FIG. 12, disposed in a second condition.
Figure 19:
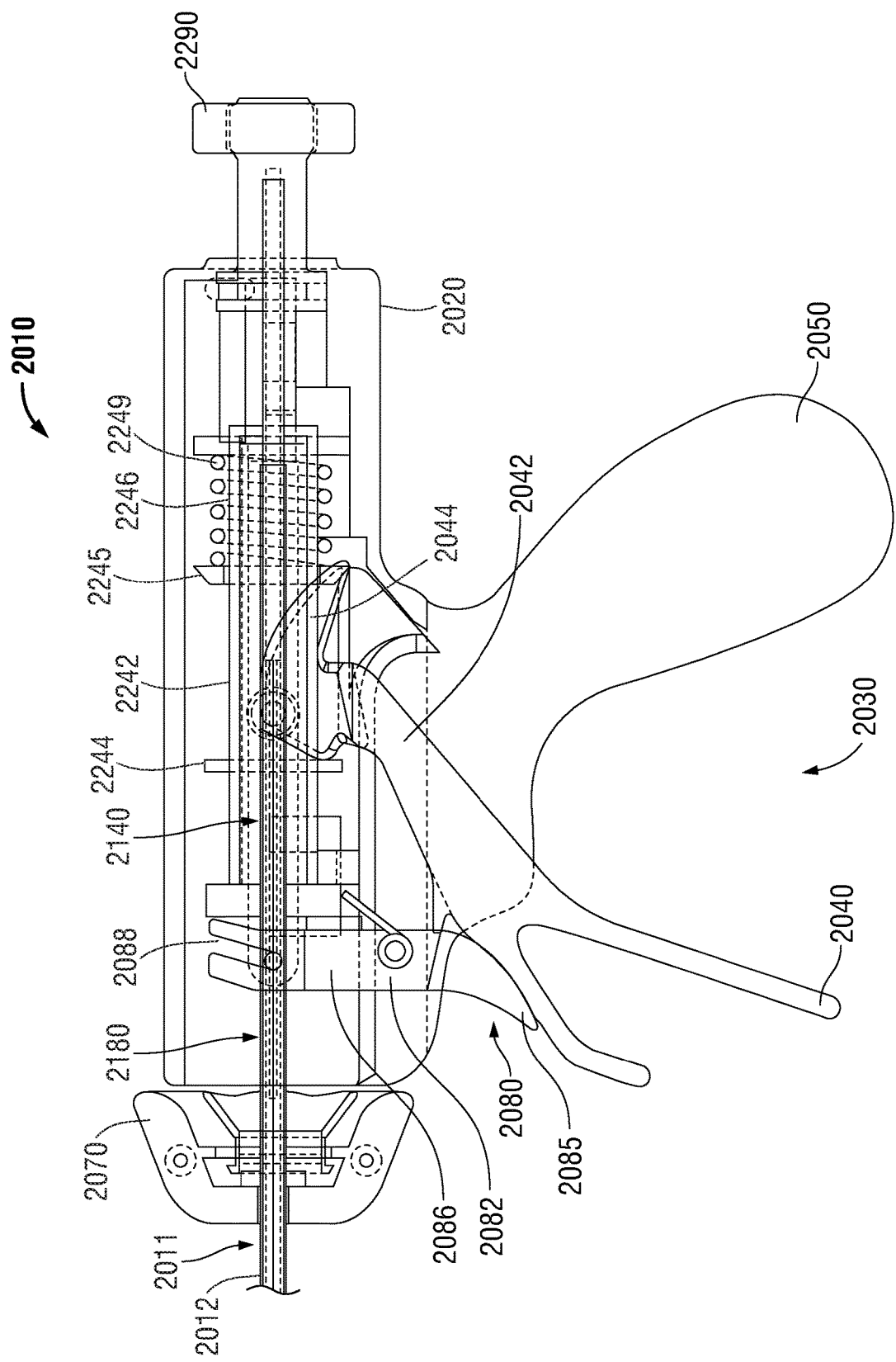
FIG. 19 is a longitudinal, cross-sectional view of the proximal end of another endoscopic surgical forceps provided in accordance with the present disclosure.
Figure 20:
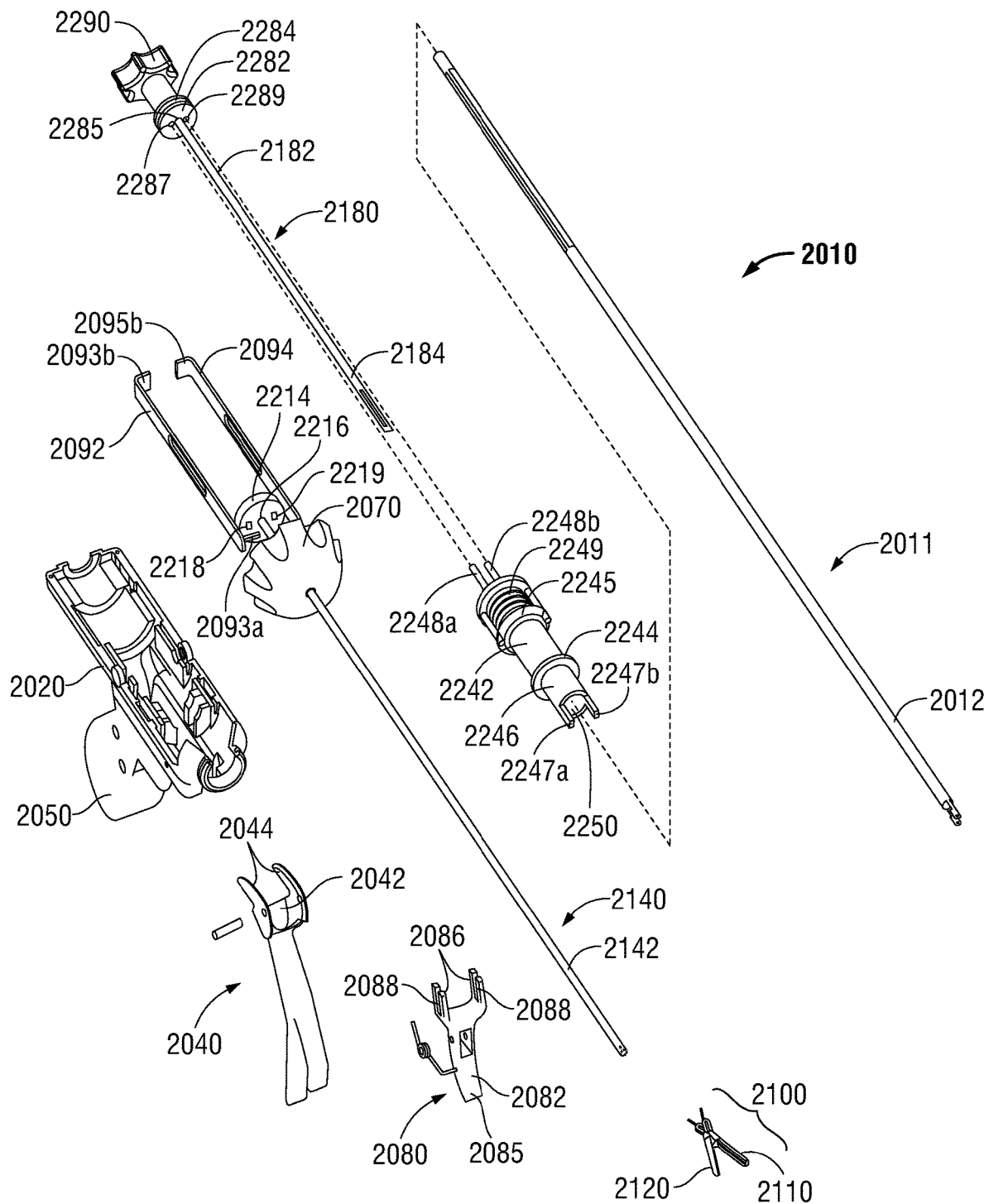
FIG. 20 is an exploded, perspective view of the forceps of FIG. 19.

Referring initially to FIGS. 12-14, forceps 1010 generally including a housing 1020, a handle assembly 1030, a rotating assembly 1070, a trigger assembly 1080, an end effector assembly 1100, and an extension mechanism 1200. Forceps 1010 further includes a shaft assembly 1011 including a shaft 1012 extending between end effector assembly 1100 and housing 1020. Shaft assembly 1011, handle assembly 1030, and trigger assembly 1080 are coupled to extension mechanism 1200 which, in turn, is configured to operably couple to a drive assembly 1140 and a knife assembly 1180 in each of a proximal, a distal position, and a plurality of intermediate positions therebetween, corresponding to the retracted, extended, and intermediate positions of forceps 1010 such that, as detailed below, and similarly as detailed above with respect to forceps 10 (FIGS. 1A-11), regardless of the position of forceps 1010, handle assembly 1030 is operable to translate drive assembly 1140 through shaft 1012 to effect pivoting of jaw members 1110, 1120 relative to one another between the spaced-apart and approximated positions, and such that trigger assembly 1080 is operably to translate knife assembly 1180 to effect deployment of the knife blade 1184 between jaw members 1110, 1120 to cut tissue grasped therebetween.

Extension mechanism 1200 includes a pair of side rails 1242, 1244 slidably supported within housing 1020, top and bottom rails 1282, 1284 slidably supported within housing 1020, a shaft coupling assembly 1211, a drive coupling assembly 1240, a knife coupling assembly 1280, and an actuation assembly 1290. Shaft coupling assembly 1211 is operably coupled to shaft assembly 1011 (see FIGS. 17A and 17B), drive coupling assembly 1240 is coupled to handle assembly 1030 and is configured for operable coupling to drive assembly 1140 (see FIGS. 18A and 18B), and knife coupling assembly 1280 is coupled to trigger assembly 1080 and is configured for operable coupling to knife assembly 1180.

Actuation assembly 1290 of extension mechanism 1200 includes an actuator 1292 that extends through a slot 1022 defined within housing 1020 of forceps 1010. Actuator 1292, as detailed below, is selectively depressible to transition extension mechanism 1200 from a use condition to an extension/retraction condition and, once disposed in the extension/retraction condition, is selectively translatable through slot 1022 and relative to housing 1020 to cooperatively move shaft assembly 1011, drive assembly 1140, and trigger assembly 1180 between their respective proximal and distal positions and any intermediate positions therebetween to transition forceps 1010 between the retracted position, the extended position, and any of the intermediate positions therebetween. Once the desired position, e.g., the retracted position, an intermediate position, or the extended position, has been achieved, extension mechanism 1200 may be transitioned to the use condition by releasing actuator 1292.

With reference to FIGS. 13-17B, shaft assembly 1011 includes shaft 1012 and a proximal rod 1014 coupled to and extending proximally from shaft 1012. Shaft 1012 extends distally from housing 1020 (FIG. 12), ultimately pivotably supporting jaw members 1110, 1120 (FIG. 12) at the distal end of shaft 1012. Shaft 1012 further defines a pair of opposed longitudinal slots 1016 (only one of which is shown) that are configured to permit coupling of knife assembly 1180 with extension mechanism 1200 and trigger assembly 1080, as detailed below. Proximal rod 1014 is coupled to shaft coupling assembly 1211 for permitting extension mechanism 1200 to transition between the use condition and the extension/retraction condition and for permitting forceps 10 to move between each of the retracted, extended, and intermediate positions. More specifically, shaft coupling assembly 1211 includes a winged lock member 1212, a biasing member 1214, and a wedge component 1216.

Winged lock member 1212 includes a body 1213*a* and a pair of wings 1213*b* disposed on either side of body 1213*a* and coupled thereto via living hinges. Wings 1213*b* are biased to extend inwardly towards one another. Wings 1213*b* and body 1213*a* cooperate to define a partially enclosed internal area 1213*c* therebetween. Biasing member 1214 is disposed within internal area 1213c. Body 1213a of winged lock member 1212 is slidably disposed about proximal rod 1014 of shaft assembly 1011. Each wing 1213b defines a foot 1213d at the free end thereof, the importance of which will be detailed below.

Wedge component 1216 of shaft coupling assembly 1211 includes a washer 1217 and a first wedge member 1218. Actuation assembly 1290 includes an actuator rod 1294 extending between and interconnecting actuator 1292 with a second wedge member 1296 shaped complementary to first wedge member 1218. In the use condition of extension mechanism 1200 (FIG. 17A) corresponding to the initial or un-depressed position of actuator 1292, first and second wedge members 1218, 1296, respectively, do not interfere with one another. As such, biasing member 1214 acts to bias wedge component 1216 proximally such that washer 1217 is positioned between feet 1213d of wings 1213b to urge and retain wings 1213b in generally perpendicular orientation relative to body 1213a of winged lock member 1212, wherein feet 1213d of wings 1213b are frictionally retained in position relative to housing 1020 between washer 1217 and internal rails 1026, 1028 (FIGS. 17A and 17B) of housing 1020. Thus, in the use condition of extension mechanism 1200 (FIG. 17A), shaft assembly 1011 is fixed position relative to housing 1020.

In the extension/retraction condition of extension mechanism 1200 (FIG. 17B) corresponding to the depressed position of actuator 1292, second wedge member 1296 is urged into contact with first wedge member 1218 and, due to the complementary shaped configurations thereof, urges first wedge member 1218 distally as actuator 1292 is depressed. Distal translation of first wedge member 1218, in turn, urges washer 1217 distally against the bias of biasing member 1214 and into internal area 1213c of winged lock member 1212 such that wings 1213b are permitted to return, under their bias, to extend inwardly towards one another. Thus, in the extension/retraction condition of extension mechanism 1200 (FIG. 17B), wings 1213b are no longer frictionally retained in position relative to housing 1020 and, thus, shaft assembly 1011 is permitted to translate longitudinally relative to housing 1020 upon similar translation of actuator 1292.

With reference to FIGS. 13-16, 18A, and 18B, drive assembly 1140 is similar to drive assembly 140 of forceps 10 (FIG. 3) and generally includes a drive bar 1142 having a transverse pin 1144 disposed at the distal end thereof for operably coupling to jaw members 1110, 1120, and a proximal hub 1146 disposed at the proximal end thereof that is configured to releasably engage drive coupling assembly 1240. Drive bar 1142 further defines a longitudinal slot 1143 towards the proximal end thereof. Proximal hub 1146 includes a pair of horizontally-oriented, opposed posts 1148 extending outwardly therefrom. Each posts 1148 is coupled to a spring arm 1149 having a distal base 1151, a proximal base 1153, and a leaf spring 1155 extending therebetween. Distal bases 1151 of spring arms 1149 are disposed about posts 1148 to couple respective spring arms 1149 to posts 1148, while proximal bases 1153 are releasably engagable with respective side rails 1242, 1244 to releasably secure drive assembly 1140 thereto in any one of the proximal, distal, or intermediate positions.

Drive coupling assembly 1240 of extension mechanism 1200 includes, as mentioned above, a pair of side rails 1242, 1244. Drive coupling assembly 1240 further includes an engagement wheel 1246 supported on proximal rod 1014 of shaft assembly 1011. As detailed below, engagement wheel 1246 also forms part of knife coupling assembly 1280. Engagement wheel 1246 defines an annular channel 1248 defining alternatingly deep and shallow steps 1249a, 1249b, respectively, and is coupled to second wedge member 1296 of actuation assembly 1290 such that depression of actuator 1292 effects rotation of engagement wheel 1246, the importance of which is detailed below.

Rails 1242, 1244 each define an internal channel 1243a, 1245a and a scalloped longitudinal slot 1243b, 1245b that provides access to respective channels 1243a, 1245a. Proximal bases 1153 of spring arms 1149 each include first, second, and third portions 1153a, 1153b, 1153c defining different dimensions. First portions 1153a are slidably received within internal channels 1243a, 1245a, respectively and are dimensioned larger than respective longitudinal slots 1243b, 1245b such that first portions 1153a are retained within respective internal channels 1243a, 1245a. Second portions 1153b extend from first portions 1153a and are dimensioned larger than each of the plurality of enlarged apertures 1243c, 1245c defined by the scalloped longitudinal slots 1243b, 1245b but smaller than the reduced portions of the scalloped longitudinal slots 1243b, 1245b defined between each of the enlarged apertures 1243c, 1245c. Thus, second portions 1153b may be retained within any one of the enlarged apertures 1243c, 1245c of the scallop-shaped longitudinal slots 1243b, 1245b, but are inhibited from translating therebetween. Third portions 1153c extend from second portions 1153b are dimensioned to freely extend through and translate along scalloped longitudinal slots 1243b, 1245b. Further, third portions 1153c are operably received within annular channel 1248 of engagement wheel 1246 on opposed sides thereof, as detailed below.

In the use condition of extension mechanism 1200 (FIG. 18A) corresponding to the initial or un-depressed position of actuator 1292, deep steps 1249a of annular channel 1248 of engagement wheel 1246 are positioned adjacent third portions 1153c of proximal bases 1153 of spring arms 1149. In this position, leaf springs 1155 bias proximal bases 1153 inwardly such that second portions 1153b extending partially through one of the plurality of enlarged apertures 1243c, 1245c defined by the scalloped longitudinal slots 1243b, 1245b of rails 1242, 1244, respectively. The particular enlarged apertures 1243c, 1245c through which second portions 1153b extend depend upon the position of forceps 1010, e.g., the retracted position, extended position, or an intermediate position therebetween. As a result of the engagement of second portions 1153b of proximal bases 1153b within enlarged apertures 1243c, 1245c, respectively, drive assembly 1140 is operably engaged with rails 1242, 1244 such that translation of rails 1242, 1244 may be effected to pivot jaw members 1110, 11120 between the spaced-apart and approximated positions, as detailed below.

In the extension/retraction condition of extension mechanism 1200 (FIG. 18B) corresponding to the depressed position of actuator 1292, the movement of second wedge member 1296 urges engagement wheel 1246 to rotate such that shallow steps 1249b of annular channel 1248 are positioned adjacent third portions 1153c of proximal bases 1153 of spring arms 1149. In this position, third portions 1153c are urged outwardly against the bias of leaf springs 1155 such that second portions 1153b of proximal bases 1153 are fully disposed within longitudinal slots 1243b, 1245b of rails 1242, 1244, respectively, and, thus, are permitted to translate therealong and relative thereto, e.g., upon translation of actuator 1292 through slot 1022 and relative to housing 1020, to permit transitioning of forceps 1010 between the retracted position, extended position, or any of the intermediate positions therebetween. Upon release of actuator 1292, engagement wheel 1246 is rotated back to its initial position such that second portions 1153b are once again biased into the adjacent enlarged aperture 1243c, 1245c to secure drive assembly 1140 relative to rails 1242, 1244 in the desired position of forceps 1010, e.g., the retracted position, extended position, or an intermediate position therebetween.

As noted above, drive coupling assembly 1240 is engaged with handle assembly 1030 such that, with drive assembly 1140 engaged with drive coupling assembly 1240, handle assembly 1030 may be manipulated to pivot jaw members 1110, 1120 relative to one another. More specifically, movable handle 1040 of handle assembly 1030 is pivotably coupled to housing 1020 on either side thereof via a split pivot 1042 and is coupled to a pair of drive lever 1044 via one or more linkages 1046. Drive levers 1044 are pivotably coupled to fixed handle 1050 at first ends thereof and are pivotably coupled to a slider 1048 on either side of extension mechanism 1200 at second ends thereof. Slider 1048 is secured about rails 1242, 1244 via engagement of posts 1249a, 1249b of rails 1242, 1244 with corresponding apertures (not explicitly shown) defined within slider 1048. Linkage 1046 is coupled to drive levers 1044 at an intermediate position between the first and second ends thereof. As a result of the above configuration, in the use condition of extension mechanism 1200 (regardless of the position of forceps 1010, e.g., the extended position, retracted position, or any intermediate position therebetween), pivoting of movable handle 1040 about split pivot 1042 and towards fixed handle 1050 urges drive levers 1044 proximally, thereby urging slider 1048 proximally and, ultimately, rails 1242, 1244 and drive bar 1142 proximally to pivot jaw members 1110, 1120 towards the approximated position. On the other hand, release or return of movable handle 1040 away from fixed handle 1050 urges slider 1048 and, ultimately, drive bar 1142 distally to pivot jaw members 1110, 1120 towards the spaced-apart position. A biasing member 1049 disposed about linkage 1046 between movable handle 1040 and drive levers 1044 is provided to bias movable handle 1040 towards its initial position, corresponding to the spaced-apart position of jaw member 1110, 1120, although other configurations are also contemplated.

With reference to FIGS. 13-16, knife assembly 1180 includes a knife drive bar 1182, knife blade 1184, and knife hub 1186. Knife blade 1184 extends distally from knife drive bar 1182. Knife hub 1186 is slidably disposed about drive bar 1142 and shaft 1012 and is coupled to the proximal end of knife drive bar 1182 via a pin 1187 which extends through longitudinal slots 1143 of drive bar 1142 of drive assembly 1140 and longitudinal slots 1016 of shaft 1012 of shaft assembly 1011. Knife hub 1186 includes a pair of vertically-oriented, opposed posts 1188 extending outwardly therefrom. Each post 1188 is coupled to a spring arm 1189, similar to spring arms 1149 of drive assembly 1140 (see FIGS. 18A and 18B). Spring arms 1189 are ultimately coupled to respective top and bottom rails 1282, 1284 and engagement wheel 1246 of knife coupling assembly 1280 of extension mechanism 1200 to releasably engage knife assembly 1180 with extension mechanism 1200 in any one of the proximal, distal, or intermediate positions. That is, the coupling of knife assembly 1280 with extension mechanism 1200 is similar to that detailed above with respect to the coupling of drive assembly 1140 and extension mechanism 1200 (see FIGS. 18A and 18B) except that, rather than being operably engagable on either side thereof, knife assembly 1280 is operably engagable with extension mechanism 1200 on the top and bottom thereof.

Trigger assembly 1080 includes a trigger 1082 pivotably coupled to housing 1020 at an intermediate portion of trigger 1082, a toggle member 1085 extending downwardly from the intermediate portion, and a pair of spaced-apart legs 1086 extending upwardly from the intermediate portion. Legs 1086 are disposed on either side of a slider 1088 that is secured about rails 1282, 1284 via engagement of posts 1289a, 1289b of rails 1282, 1284 with corresponding apertures (not explicitly shown) defined within slider 1088. As a result of this configuration, in the use condition of extension mechanism 1200 (regardless of the position of forceps 1010, e.g., the extended position, retracted position, or any intermediate position therebetween), actuation of trigger 1082 urges slider 1088 distally and, ultimately, rails 1282, 1284 and knife drive bar 1182 distally to translate knife blade 1184 from the storage position to the deployed position. On the other hand, release or return of trigger 1082 urges slider 1088 and, ultimately, knife drive bar 1182 proximally to return knife blade 1184 to the storage position. Knife blade 1184 may be biased towards the storage condition, although other configurations are also contemplated.

With respect to the use and operation of forceps 1010, referring generally to FIGS. 12-14, initially, the desired position of forceps 1010 is determined. In order to transition forceps 1010 to the desired position, actuator 1292 is initially depressed to achieve the extension/retraction condition of extension assembly 1200, wherein shaft assembly 1011 is disengaged from housing 1020, drive assembly 1140 is disengaged from rails 1242, 1244, and knife assembly 1180 is disengaged from rails 1282, 1284. Thereafter, actuator 1292 may be translated through slot 1022 and relative to housing 1020 to move shaft assembly 1011, drive assembly 1140, and knife assembly 1180 in conjunction with one another to a desired position, e.g., proximal position, distal position, or intermediate position therebetween, thus transitioning forceps 10 between the retracted position, extended position, or an intermediate position therebetween. Once the desired position has been achieved, actuator 1292 is released or returned to the initial, un-depressed position corresponding to the use condition of extensions assembly 1200, wherein shaft assembly 1011 is engaged with housing 1020, drive assembly 1140 is engaged with rails 1242, 1244, and knife assembly 1180 is engaged with rails 1282, 1284. The use and operation of forceps 1010 is otherwise similar to that detailed above with respect to forceps 10 (FIGS. 1A-11).

Turning now to FIGS. 19-22, another embodiment of a forceps 2010 provided in accordance with the present disclosure is shown. Similar to forceps 10 (FIGS. 1A-11), forceps 2010 is transitionable between and operable in each of a retracted position and an extended position. Further, forceps 2010 is continuously transitionable between and operable in each of the retracted position, the extended position, and any position therebetween. For purposes of brevity, only the differences between forceps 2010 and forceps 10 (FIGS. 1A-11) will be described in detail below, while similarities will only be summarily described or omitted entirely.

Forceps 2010 generally including a housing 2020, a handle assembly 2030, a rotating assembly 2070, a trigger assembly 2080, an end effector assembly 2100, and an extension mechanism 2200. Handle assembly 2030 and trigger assembly 2080 are operably coupled to a drive assembly 2140 and a knife assembly 2180, respectively, via extension mechanism 2200. Forceps 2010 further includes a shaft assembly 2011 that is also operably coupled to extension mechanism 2200.

Handle assembly 2030 includes a movable handle 2040 that is pivotably coupled to housing 2020 and a fixed handle 2050 that is integrally associated with housing 2020. Movable handle 2040 defines a bifurcated portion 2042 that extends into housing 2020. Bifurcated portion 2042 defines a pair of spaced-apart thumbs 2044 that are operably positioned between raised portions 2244, 2245 of sleeve 2242 of extension mechanism 2200. Extension mechanism 2200 further includes a drive tube 2246 having a first pair of spaced-apart fingers 2247a, 2247b extending proximally therefrom and a second pair of spaced-apart fingers 2248a, 2248b extending distally therefrom. Sleeve 2242 is slidably disposed about drive tube 2246. A biasing member 2249 is disposed between sleeve 2242 and the distal end of drive tube 2246 to bias sleeve 2242 distally, thereby biasing movable handle 2040 towards an initial position wherein movable handle 2040 is spaced-apart from fixed handle 2050. Upon compression of movable handle 2040 relative to fixed handle 2050, sleeve 2242 and drive tube 2246 are translated proximally and, upon release of movable handle 2040, are returned under bias distally. Drive tube 2246 defines an interior lumen 2250 that includes threading 2252 disposed on the interior surface thereof, the importance of which will be detailed below.

Drive assembly 2140, similarly as detailed above with respect to the previous embodiments, includes a drive bar 2142 that is operably coupled to jaw members 2110, 2120 of end effector assembly 2100 at the distal end thereof such that translation of drive bar 2142 effects pivoting of jaw members 2110, 2120 between the spaced-apart and approximated positions. The proximal end of drive bar 2142 defines threading 2152 on the outer surface thereof. The proximal end of drive bar 2142 extends through interior lumen 2250 of drive tube 2246 with threading 2152 operably engaged with threading 2252. As a result of this configuration, upon compression of movable handle 2040 relative to fixed handle 2050, drive bar 2142 is translated proximally to approximate jaw members 2110, 2120, while, upon release or return of movable handle 2040, drive bar 2142 is translated distally to return jaw members 2110, 2120 towards the spaced-apart position.

Trigger assembly 2080 includes a trigger 2082 that is pivotably coupled to housing 2020 about an intermediate portion of trigger 2082. Trigger 2082 includes a toggle member 2085 that extends downwardly from the intermediate portion and a pair of spaced-apart legs 2086 that extend upwardly from the intermediate portion. Legs 2086 each define a slot 2088 extending therethrough. Trigger assembly 2080 further includes a pair of connector arms 2092, 2094 each including a proximal pin 2093a, 2095a extending inwardly from the proximal end thereof and a distal end 2093b, 2095b that angled inwardly to oppose the angled distal end 2095b, 2093b of the other connector arm 2094, 2092, respectively. Proximal pins 2093a, 2095a are configured for receipt within slots 2088 of legs 2086 of trigger 2082. Angled distal ends 2093b, 2095b are configured for receipt within annular channel 2284 defined within collar 2282 of extension mechanism 2200. Thus, actuation of trigger 2082 urges connector arms 2092, 2094 and collar 2282 distally while return of trigger 2082 returns connector arms 2092, 2094 and collar 2282 proximally.

Collar 2282 defines a central aperture 2285 that includes threading 2286 disposed on the interior surface thereof, the importance of which will be detailed below. Collar 2282 further includes a pair of off-centered apertures 2287, 2289 defined therethrough on opposing sides of central aperture 2285 that are configured to slidably receive second pair of spaced-apart fingers 2248a, 2248b. As a result, collar 2282 and drive tube 2246 are rotatably fixed relative to one another. A rotation knob 2290 of extension mechanism 2200 extends proximally from collar 2282 and is positioned externally of housing 2020 to permit manual manipulation of rotation knob 2290.

Knife assembly 2180, similar as detailed above with respect to the previous embodiments, includes a knife drive bar 2182 having a knife blade 2184 extending distally therefrom. Knife drive bar 2182 is translatable through drive bar 2142 and relative to end effector assembly 2100 to translate knife blade 2184 between the storage position and the deployed position. The proximal end of knife drive bar 2182 defines threading 2186 on the outer surface thereof. The proximal end of knife drive bar 2182 extends through central aperture 2285 of collar 2282 with threading 2186 operably engaged with threading 2286. As a result of this configuration, actuation of trigger 2082 translates knife blade 2184 towards the deployed position while release or return of trigger 2082 translates knife blade 2184 back towards the storage position.

A proximal hub 2214 of extension mechanism 2200 defines a central aperture 2216 that includes threading 2217 disposed on the interior surface thereof, the importance of which will be detailed below. Proximal hub 2214 further includes a pair of off-centered apertures 2218, 2219 defined therethrough on opposes sides of central aperture 2216 that are configured to slidably receive first pair of spaced-apart fingers 2247a, 2247b. As a result, proximal hub 2214, collar 2282, and drive tube 2246 are rotatably fixed relative to one another.

Shaft assembly 2011 includes a shaft 2012 configured to pivotably engage jaw members 2110, 2120 of end effector assembly 2100 thereto at the distal end of shaft 2012 and a proximal end defining threading 2017 on the outer surface thereof. The proximal end of shaft 2012 extends through central aperture 2216 of proximal hub 2214 with threading 2017 operably engaged with threading 2217.

Figure 21:
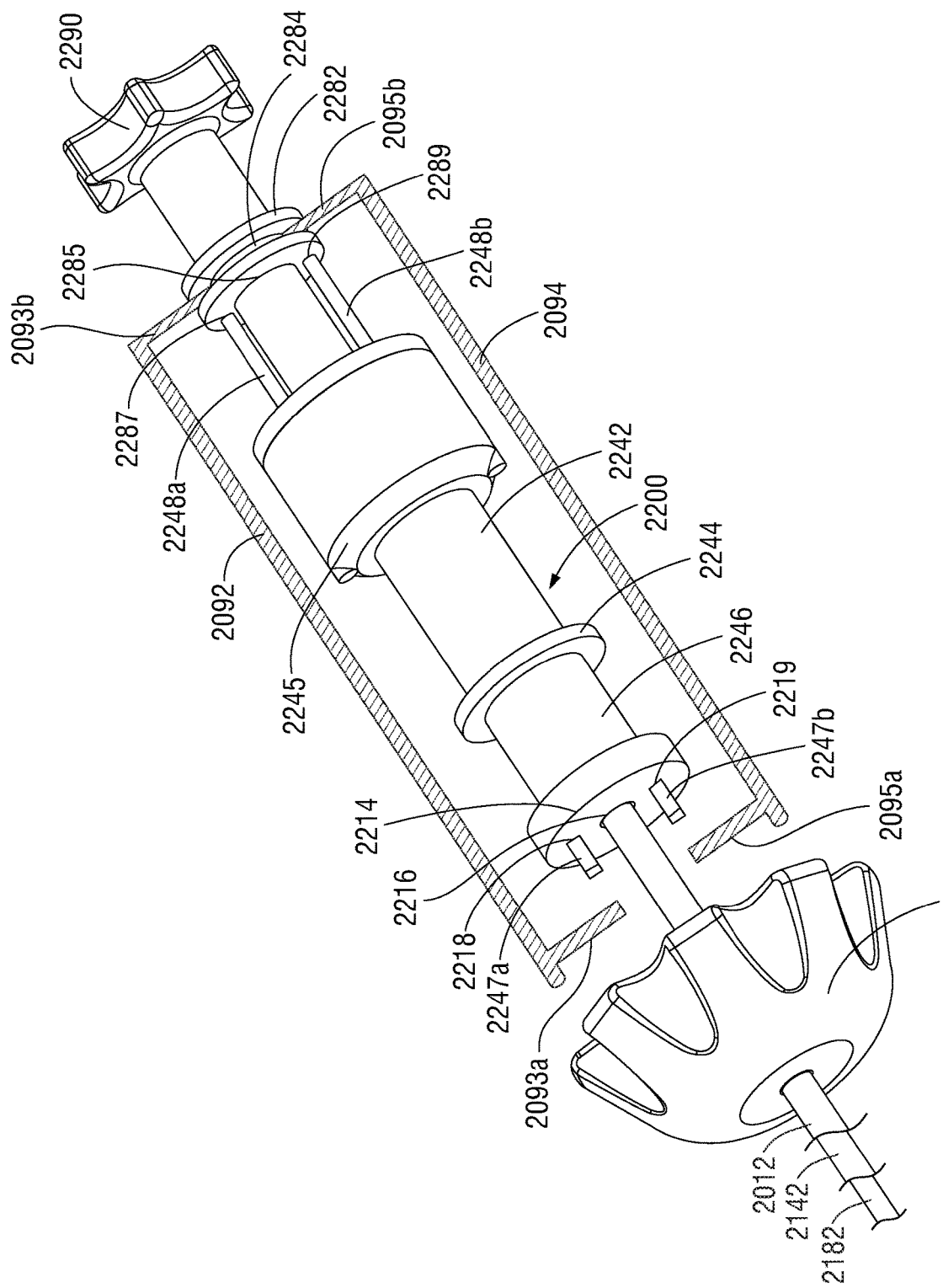
FIG. 21 is a perspective view of the internal operable assemblies of the forceps of FIG. 19.
Figure 22:
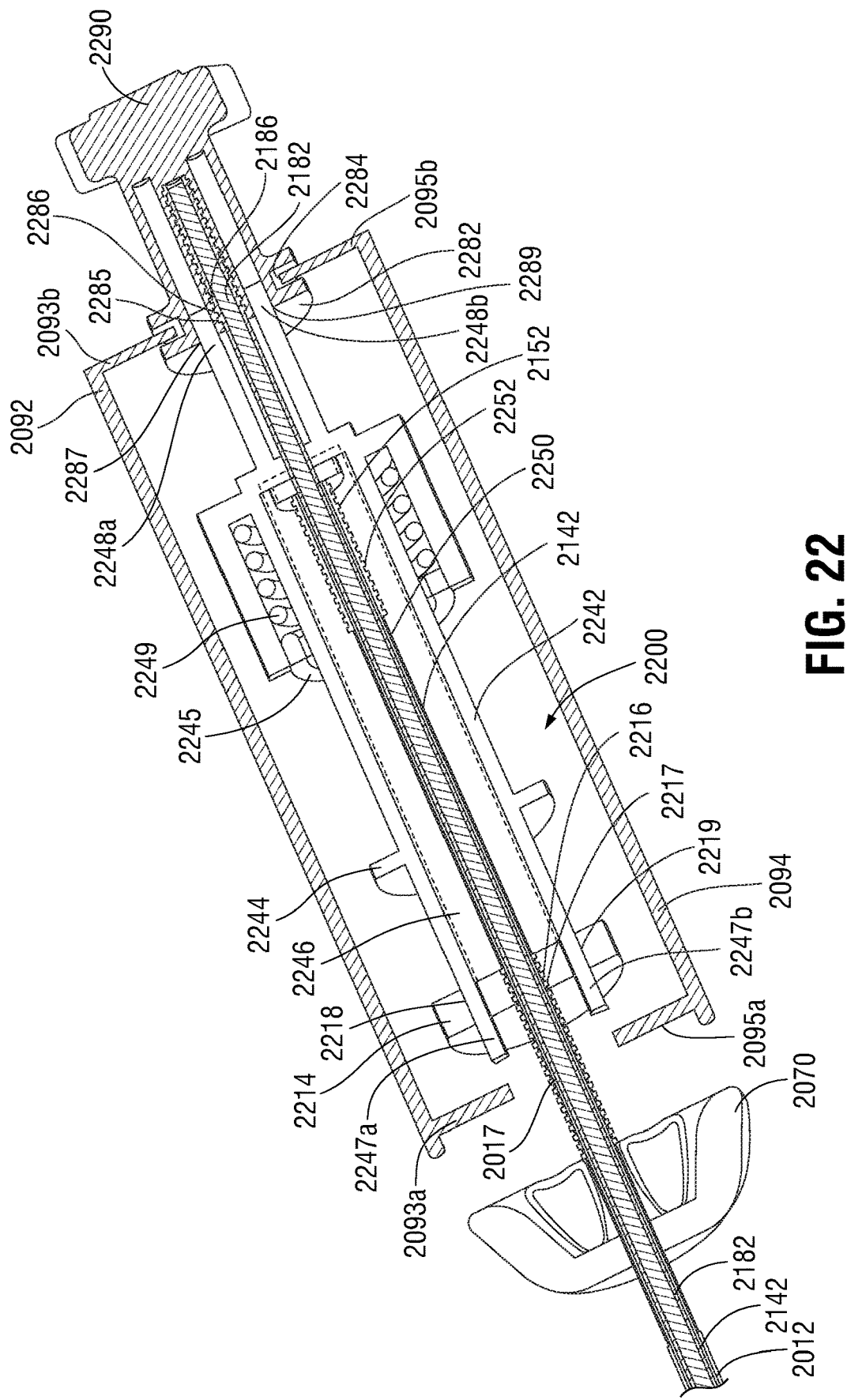
FIG. 22 is a longitudinal, cross-sectional view of the internal operable assemblies of the forceps of FIG. 19.

With particular reference to FIGS. 21 and 22, as noted above, shaft 2012 is threadingly engaged with proximal hub 2214, drive bar 2142 is threadingly engaged with drive tube 2246, and knife drive bar 2182 is threadingly engaged with collar 2282. These threading engagements are respectively pitched such that rotation of proximal hub 2214 effects rotation and translation of shaft 2012, such that rotation of drive tube 2246 effects rotation and translation of drive bar 2142, and such that rotation of collar 2282 effects rotation and translation of knife drive bar 2182. As also noted above, first pair of spaced-apart fingers 2247a, 2247b of drive tube 2246 are received within off-centered apertures 2218, 2219 of proximal hub 2214 and second pair of spaced-apart fingers 2248a, 2248b of drive tube 2246 are received within off-centered apertures 2287, 2289 of collar 2282 to rotatably fix proximal hub 2214, collar 2282, and drive tube 2246 relative to one another. Thus, cooperative translation of shaft assembly 2011, drive assembly 214, and knife assembly 2180 between their respective proximal, distal, and intermediate positions, corresponding to the retracted, extended, and intermediate positions of forceps 2010, may be effected by rotating rotation knob 2290, which extends from collar 2282.

The use and operation of forceps 2010 is similar to that of the previous embodiments except for the extension and retraction thereof, which, as detailed above, is effected via rotation of rotation knob 2290 relative to housing 2020.

The above-detailed embodiments may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a housing;
a shaft extending distally from the housing, the shaft having a fixed length and including a proximal end portion extending into and movably engaged with the housing;
an end effector assembly disposed at a distal end of the shaft;
a movable handle coupled to the housing;
a drive assembly coupled to the end effector assembly; and
an extension mechanism disposed within the housing, the extension mechanism directly coupled to the proximal end portion of the shaft, the extension mechanism configured to simultaneously move the shaft, the drive assembly, and the end effector assembly relative to the housing between a retracted position, wherein each of the shaft, the drive assembly, and the end effector assembly extends a first distance from the housing, and an extended position, wherein each of the shaft, the drive assembly, and the end effector assembly extends a second, different distance from the housing, the extension mechanism coupled between the movable handle and the drive assembly in each of the retracted and extended positions such that the movable handle is operable to effect manipulation of the end effector assembly in each of the retracted and extended positions.

2. The surgical instrument according to claim 1, wherein the extension mechanism is further configured to incrementally move the shaft, the drive assembly, and the end effector assembly relative to the housing between a plurality of discrete intermediate positions disposed between the retracted position and the extended position, and wherein the extension mechanism is coupled between the movable handle and the drive assembly in each of the intermediate positions such that the movable handle is operable to effect manipulation of the end effector assembly in each of the intermediate positions.

3. The surgical instrument according to claim 1, wherein the extension mechanism is further configured to continuously move the shaft, the drive assembly, and the end effector assembly relative to the housing between the retracted position, the extended position, and intermediate positions therebetween, and wherein the extension mechanism is coupled between the movable handle and the drive assembly in each of the intermediate positions such that the movable handle is operable to effect manipulation of the end effector assembly in each of the intermediate positions.

4. The surgical instrument according to claim 1, wherein the extension mechanism is transitionable between a use condition, wherein the shaft is retained in substantially fixed position relative to the housing and the drive assembly is coupled to the movable handle, and an extension/retraction condition, wherein the shaft is movable relative to the housing and the drive assembly is decoupled from the movable handle.

5. The surgical instrument according to claim 4, wherein the extension mechanism further includes an actuator translatable along the housing between a proximal position and a distal position for moving the shaft, the drive assembly, and the end effector assembly between the retracted position and the extended position.

6. The surgical instrument according to claim 5, wherein, in each of the proximal and distal positions, the actuator is rotatable relative to the housing for transitioning the extension mechanism between the use condition and the extension/retraction condition.

7. The surgical instrument according to claim 5, wherein the extension mechanism further includes a rotation knob that is selectively rotatable relative to the housing for transitioning the extension mechanism between the use condition and the extension/retraction condition.

8. The surgical instrument according to claim 1, wherein the extension mechanism further includes a rotatable actuator coupled to the shaft and the drive assembly, the rotatable actuator selectively rotatable relative to the housing for moving the shaft and drive assembly between the retracted position and the extended position.

9. A surgical instrument, comprising:
a housing;
a shaft extending distally from the housing, the shaft having a fixed length and including a proximal end portion extending into and movably engaged with the housing;
an end effector assembly disposed at a distal end of the shaft, the end effector assembly including first and second jaw members pivotable relative to one another between a spaced-apart position and an approximated position for grasping tissue therebetween;
a knife blade disposed within the shaft and translatable relative to the shaft between a storage position, wherein the knife blade is positioned proximally of the first and second jaw members, and a deployed position, wherein the knife blade extends between the first and second jaw members for cutting tissue grasped therebetween;
a movable handle coupled to the housing;
a drive assembly coupled to at least one of the first and second jaw members of the end effector assembly;
a trigger coupled to the housing;
a knife assembly coupled to the knife blade; and
an extension mechanism disposed within the housing, the extension mechanism directly coupled to the proximal end portion of the shaft, the extension mechanism configured to simultaneously move the shaft, the drive assembly, the end effector assembly, and the knife assembly relative to the housing between a retracted position, wherein each of the shaft, the drive assembly, the end effector assembly, and the knife assembly extends a first distance from the housing, and an extended position, wherein each of the shaft, the drive assembly, the end effector assembly, and the knife assembly extends a second, different distance from the housing, the extension mechanism coupled between the movable handle and the drive assembly and between the trigger and the knife assembly in each of the retracted and extended positions such that the movable handle is operable to effect relative pivoting of the first and second jaw members of the end effector assembly in each of the retracted and extended positions, and such that the trigger is operable to effect translation of the knife blade in each of the retracted and extended positions.

10. The surgical instrument according to claim 9, wherein the extension mechanism is further configured to incrementally move the shaft, the drive assembly, the end effector assembly, and the knife assembly relative to the housing between a plurality of discrete intermediate positions disposed between the retracted position and the extended position, wherein the extension mechanism is coupled between the movable handle and the drive assembly and between the trigger and the knife assembly in each of the intermediate positions such that the movable handle is operable to effect relative pivoting of the first and second jaw members of the end effector assembly in each of the intermediate positions, and such that the trigger is operable to effect translation of the knife blade in each of the intermediate positions.

11. The surgical instrument according to claim 9, wherein the extension mechanism is further configured to continuously move the shaft, the drive assembly, the end effector assembly, and the knife assembly relative to the housing between the retracted position, the extended position, and intermediate positions therebetween, wherein the extension mechanism is coupled between the movable handle and the drive assembly and between the trigger and the knife assembly in each of the intermediate positions such that the movable handle is operable to effect relative pivoting of the first and second jaw members of the end effector assembly in each of the intermediate positions, and such that the trigger is operable to effect translation of the knife blade in each of the intermediate positions.

12. The surgical instrument according to claim 9, wherein the extension mechanism is transitionable between a use condition, wherein the shaft is retained in substantially fixed position relative to the housing, the drive assembly is coupled to the movable handle via the extension mechanism, and the knife assembly is coupled to the trigger via the extension mechanism, and an extension/retraction condition, wherein the shaft is movable relative to the housing, the drive assembly is decoupled from the movable handle, and the knife assembly is decoupled from the trigger.

13. The surgical instrument according to claim 12, wherein the extension mechanism further includes an actuator translatable along the housing between a proximal position and a distal position for moving the shaft, the drive assembly, the end effector assembly, and the knife assembly between the retracted position and the extended position.

14. The surgical instrument according to claim 13, wherein, in each of the proximal and distal positions, the actuator is rotatable relative to the housing for transitioning the extension mechanism between the use condition and the extension/retraction condition.

15. The surgical instrument according to claim 13, wherein the extension mechanism further includes a rotation knob that is selectively rotatable relative to the housing for transitioning the extension mechanism between the use condition and the extension/retraction condition.

16. The surgical instrument according to claim 9, wherein the extension mechanism further includes a rotatable actuator coupled to the shaft, the drive assembly, the end effector assembly, and the knife assembly, the rotatable actuator selectively rotatable relative to the housing for moving the shaft, the drive assembly, the end effector assembly, and the knife assembly between the retracted position and the extended position.

17. The surgical instrument according to claim 9, wherein the first and second jaw members of the end effector assembly are adapted to connect to a source of energy for treating tissue grasped therebetween.

18. The surgical instrument according to claim 9, wherein the extension mechanism includes a set of concentric tube members, each tube member of the set of concentric tube members directly and operably coupled to one of the shaft, the knife assembly, or the drive assembly.

19. The surgical instrument according to claim 1, wherein the extension mechanism includes a set of concentric tube members, one tube member of the set of concentric tube members directly and operably coupled to the shaft and another tube member of the set of concentric tube members directly and operably coupled to the drive assembly.

20. The surgical instrument according to claim 1, wherein the extension mechanism is disposed entirely within the housing.

21. The surgical instrument according to claim 1, wherein the drive assembly is slidably disposed within the shaft and includes a proximal end portion directly coupled to the extension mechanism.

\* \* \* \* \*